United States Patent
Ro

(10) Patent No.: US 12,031,134 B2
(45) Date of Patent: Jul. 9, 2024

(54) KLF11 siRNA FOR TREATMENT OF DIABETES AND OBESITY

(71) Applicant: NEVADA RESEARCH & INNOVATION CORPORATION, Reno, NV (US)

(72) Inventor: Seungil Ro, Reno, NV (US)

(73) Assignee: Nevada Research & Innovation Corporation, Reno, NV (US)

(*) Notice: Subject to any disclaimer, the term of this patent is extended or adjusted under 35 U.S.C. 154(b) by 0 days.

(21) Appl. No.: 17/401,200

(22) Filed: Aug. 12, 2021

(65) Prior Publication Data
US 2022/0049254 A1  Feb. 17, 2022

Related U.S. Application Data

(60) Provisional application No. 63/065,242, filed on Aug. 13, 2020.

(51) Int. Cl.
  *C12N 15/113* (2010.01)
  *A61K 31/713* (2006.01)
  *A61P 3/10* (2006.01)

(52) U.S. Cl.
  CPC .......... *C12N 15/113* (2013.01); *A61K 31/713* (2013.01); *A61P 3/10* (2018.01)

(58) Field of Classification Search
  CPC ........ C12N 15/113; A61K 31/713; A61P 3/10
  See application file for complete search history.

(56) References Cited

U.S. PATENT DOCUMENTS

| | | | |
|---|---|---|---|
| 7,691,997 B2* | 4/2010 | Khvorova | C12Y 502/01008 536/24.5 |
| 2008/0113351 A1 | 5/2008 | Naito et al. | |
| 2009/0156524 A1* | 6/2009 | Feinstein | A61P 11/00 435/320.1 |
| 2009/0192114 A1* | 7/2009 | Ovcharenko | C12N 15/113 514/44 R |
| 2010/0215660 A1* | 8/2010 | Hashmi | C12N 15/113 435/325 |
| 2017/0247694 A1 | 8/2017 | Mamet et al. | |

OTHER PUBLICATIONS

Sharfstein, Non-protein biologic therapeutic, 2018, Current Opinion in Biotechnology, 53:65-75 (Year: 2018).*
Fan et al., Krüppel Like Factor 11, a Transcription Factor Involved in Diabetes, Suppresses Endothelial Cell Activation via the NF-κB signaling pathway, 2012, Arterioscler. Thromb. Vasc. Biol., 32, 12, 2981-2988, (Year: 2012).*
Lin et al., The Distinct Roles of Transcriptional Factor KLF11 in Normal Cell Growth Regulation and Cancer as a Mediator of TGF-Signaling Pathway, 2020, Int. J. Mol. Sci. 21, 2928, 1-15 (Year: 2020).*
Braicu et al. The Function of Non-coding RNAs in lung cancer tumorigenesis, 2019, Cancers, 11, 1-18. (Year: 2019).*

(Continued)

*Primary Examiner* — J. E. Angell
*Assistant Examiner* — Keyur A Vyas
(74) *Attorney, Agent, or Firm* — Saul Ewing LLP; Kathryn Doyle; Lukas Pfannenstiel

(57) ABSTRACT

The present invention relates to methods and compositions comprising an inhibitor of KLF11 signaling for treatment of gastrointestinal motility disorders, obesity and diabetes.

2 Claims, 18 Drawing Sheets

Specification includes a Sequence Listing.

(56) References Cited

OTHER PUBLICATIONS

International Search Report and Written Opinion dated Feb. 9, 2022, PCT/US21/45804.
Mathison, et al., "Phenotypic Characterization of Mice Carrying Homozygous Deletion of KLF11, a Gene in which Mutations Cause Human Neonatal and Mody VII Diabetes", Endocrinology, Oct. 2015, 156(10): 3581-3595.
Qiu, et al., "Gene therapy for C1 esterase inhibitor deficiency in a Murine Model of Hereditary angioedema", Allergy, Jun. 2019; 74(6): 1081-1089.
Yin, et al., "Transcription Factor KLF11 Integrates Progesterone Receptor Signaling and Proliferation in Uterine Leiomyoma Cells", Cancer Res, Feb. 15, 2010, 70(4): 1722-1730.

\* cited by examiner siKlf11-1   GUCCUUCCCAAGUAGUUAtt  SEQ ID NO: 1
            ||||||||||||||||||||
            gaCAAGGAAGGGUUCAUCAAU  SEQ ID NO: 2 siKlf11-2   UCUGAUUUCUGUCCCUGUAtt  SEQ ID NO: 3
            ||||||||||||||||||||
            ggAGACUAAAGACAGGGACAU  SEQ ID NO: 4

FIG. 1A siKLF11-1   ACAGUUUACUCAGCACUAAtt  SEQ ID NO: 5
            ||||||||||||||||||||
            ccUGUCAAAUGAGUCGUGAUU  SEQ ID NO: 6 siKLF11-2   CACCUGAACUACCAAAAGAtt  SEQ ID NO: 7
            ||||||||||||||||||||
            gtGUGGACUUGAUGGUUUUCU  SEQ ID NO: 8

FIG. 1B

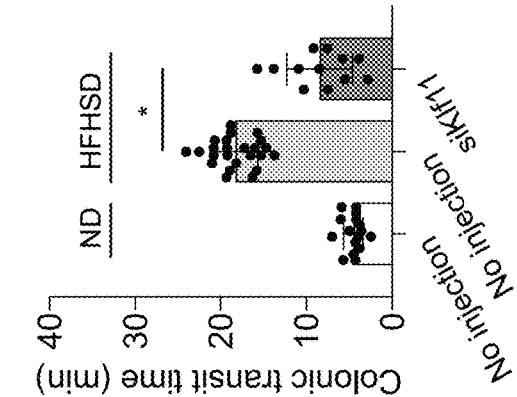
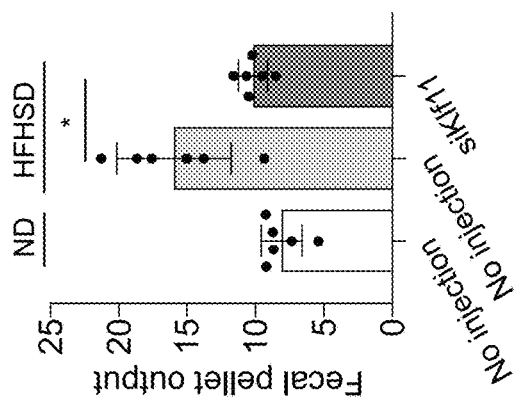
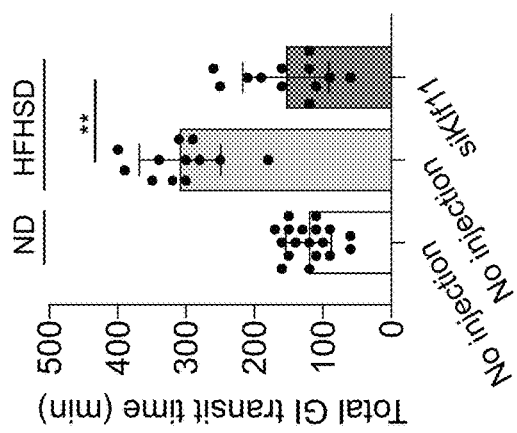
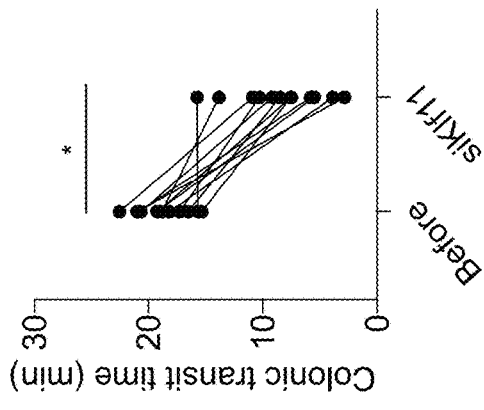
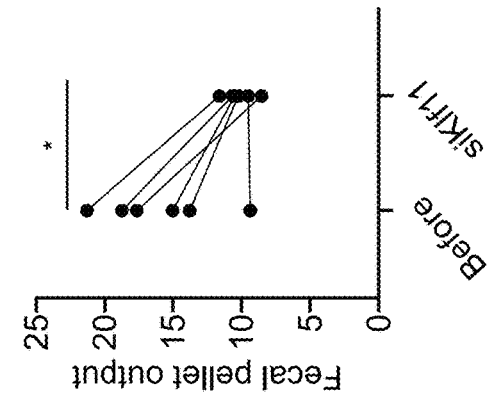
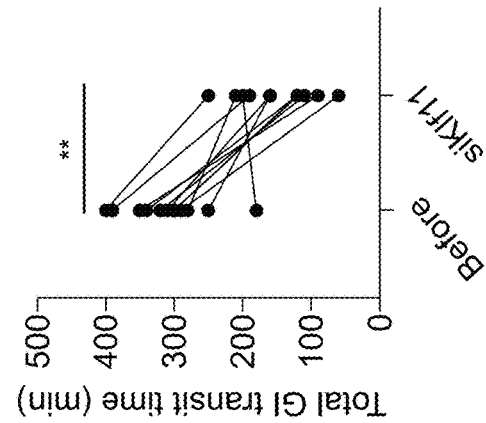

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: siKlf11-1
<220> FEATURE:
<221> NAME/KEY: misc_feature
<222> LOCATION: (1)..(21)
<223> OTHER INFORMATION: DNA/RNA sequence

<400> SEQUENCE: 1
guuccuuccc aaguaguuat t                                           21

<210> SEQ ID NO 2
<211> LENGTH: 21
<212> TYPE: RNA
<213> ORGANISM: Artificial Sequence
<220> FEATURE:
<223> OTHER INFORMATION: siKlf11-1

<400> SEQUENCE: 2
gacaaggaag gguucaucaa u                                           21

<210> SEQ ID NO 3
<211> LENGTH: 21
<212> TYPE: DNA
<213> ORGANISM: Artificial Sequence
<220> FEATURE:
<223> OTHER INFORMATION: siKlf11-2
<220> FEATURE:
<221> NAME/KEY: misc_feature
<222> LOCATION: (1)..(21)
<223> OTHER INFORMATION: DNA/RNA sequence

<400> SEQUENCE: 3
ucugauuucu gucccuguat t                                           21

<210> SEQ ID NO 4
<211> LENGTH: 21
```

```
<212> TYPE: RNA
<213> ORGANISM: Artificial Sequence
<220> FEATURE:
<223> OTHER INFORMATION: siKlf11-2

<400> SEQUENCE: 4
ggagacuaaa gacagggaca u                                              21

<210> SEQ ID NO 5
<211> LENGTH: 21
<212> TYPE: DNA
<213> ORGANISM: Artificial Sequence
<220> FEATURE:
<223> OTHER INFORMATION: siKLF11-1
<220> FEATURE:
<221> NAME/KEY: misc_feature
<223> OTHER INFORMATION: DNA/RNA Sequence

<400> SEQUENCE: 5
acaguuuacu cagcacuaat t                                              21

<210> SEQ ID NO 6
<211> LENGTH: 21
<212> TYPE: RNA
<213> ORGANISM: Artificial Sequence
<220> FEATURE:
<223> OTHER INFORMATION: siKLF11-1

<400> SEQUENCE: 6
ccugucaaau gagucgugau u                                              21

<210> SEQ ID NO 7
<211> LENGTH: 21
<212> TYPE: DNA
<213> ORGANISM: Artificial Sequence
<220> FEATURE:
<223> OTHER INFORMATION: siKLF11-2
<220> FEATURE:
<221> NAME/KEY: misc_feature
<223> OTHER INFORMATION: DNA/RNA Sequence

<400> SEQUENCE: 7
caccugaacu accaaaagat t                                              21

<210> SEQ ID NO 8
<211> LENGTH: 23
<212> TYPE: DNA
<213> ORGANISM: Artificial Sequence
<220> FEATURE:
<223> OTHER INFORMATION: siKLF11-2
<220> FEATURE:
<221> NAME/KEY: misc_feature
<223> OTHER INFORMATION: DNA/RNA Sequence

<400> SEQUENCE: 8
gtguguggac uugaugguuu ucu                                            23
```

KLF11 siRNA FOR TREATMENT OF DIABETES AND OBESITY

CROSS REFERENCE TO RELATED APPLICATION

The present application is entitled to priority under 35 U.S.C. § 119(e) to U.S. Provisional Patent Application No. 63/065,242, filed Aug. 13, 2020, which is hereby incorporated by reference in its entirety herein.

REFERENCE TO AN ELECTRONIC SEQUENCE LISTING

The contents of the electronic sequence listing (created on Jun. 26, 2023 named "369055_7017US1_ReplacementSequenceListing_ST25.txt", and 2,131 bytes in size) is herein incorporated by reference in its entirety.

BACKGROUND OF THE INVENTION

According to data from the World Health Organization, there are over 425 million diabetic patients worldwide, and that number has been rapidly increasing as the prevalence of obesity also increases. Approximately 90% of diabetics are obese demonstrating that there is a large co-occurrence of obesity and diabetes. Type 2 diabetes (T2D), a complex and heterogeneous polygenic disease, is known as adult diabetes since it mainly occurs in adults over 40 years old. T2D accounts for up to 95% of all diagnosed cases of diabetes. Unfortunately, development of effective treatments for T2D have been difficult because the pathophysiologic mechanisms underlying the disease remain elusive. Interestingly, about half of diabetic patients also have gastrointestinal (GI) complications, including gastroparesis. It is known that an abnormally high blood glucose level (hyperglycemia), a hallmark sign of diabetes, leads to gastroparesis.

KLF11 or kruppel-like factor 11 is in a family of zinc-finger transcription regulating genes. KLF11 typically binds to GC-rich DNA sequences and acts as a transcriptional repressor. Recent studies have identified KLF11 as being able to interact with the insulin promoter, where it binds both GC boxes and CACCC boxes (Niu 2007; Neve 2005) and suppresses transcriptional activation of the target gene (Niu 2007). Thus, KLF11 plays a key role in blood sugar regulation and other metabolic processes. The identification of KLF11's ability to regulate insulin expression also suggested a role in regulating other metabolic-related genes, particularly INS-interacting genes such as INSR, IRS1, IRS2, KIT, NEUROG3, SLC2A4, and GLP1R; the promoters of which contain GC-rich CpG islands and are potential KLF11 targets.

There remains a great need for improved methods and compositions to treat and prevent type 2 diabetes and related disorders including, obesity, diabetic fatty liver disease, and GI complications through the inhibition of KLF11 expression. The current invention addresses this need.

SUMMARY OF THE INVENTION

As described herein, the present invention relates to methods and compositions useful for inhibition of the expression of the gene Kruppel-like factor 11 (KLF11) in order to reduce body fat and weight, restore glucose homeostasis and insulin sensitivity, and improve gastrointestinal (GI) functions in subjects in need thereof.

As such, in one aspect, the invention includes a method of treating diabetes in a subject in need thereof, comprising administering to the subject an effective amount of an inhibitor of KLF11 signaling, thereby treating diabetes.

In certain embodiments, the inhibitor of KLF11 signaling is a small, non-coding RNA molecule.

In certain embodiments, the small, non-coding RNA molecule is selected from the group consisting of an shRNA, an siRNA, and an miRNA.

In certain embodiments, the small, non-coding RNA molecule is an siRNA.

In certain preferred embodiments, the siRNA is encoded by a nucleotide sequence selected from the group consisting of SEQ ID NOs: 1-8, or combinations thereof.

In certain embodiments, the diabetes is type 2 diabetes.

In certain embodiments, the inhibitor of KLF11 signaling further comprises a pharmaceutically acceptable carrier or adjuvant.

In another aspect, the invention includes a method of reducing body weight in a subject in need thereof, comprising administering an effective amount of an inhibitor of KLF11 signaling, thereby reducing the body weight in the subject.

In another aspect, the invention includes a method of reducing blood glucose in a subject in need thereof, the method comprising administering an effective amount of an inhibitor of KLF11 signaling, thereby lowering blood glucose in the subject.

In another aspect, the invention includes a method for increasing insulin sensitivity in a subject in need thereof, comprising administering an effective amount of an inhibitor of KLF11 signaling, thereby increasing insulin sensitivity.

In certain embodiments, the inhibitor of KLF11 signaling is a small, non-coding RNA molecule.

In certain embodiments, the small, non-coding RNA molecule is selected from the group consisting of an shRNA, an siRNA, and an miRNA.

In certain embodiments, the small, non-coding RNA molecule is an siRNA.

In certain preferred embodiments, the siRNA is encoded by a nucleotide sequence selected from the group consisting of SEQ ID NOs: 1-8 or combinations thereof.

In certain embodiments, the inhibitor of KLF11 signaling further comprises a pharmaceutically acceptable carrier or adjuvant.

In another aspect, the invention includes a method of treating gastrointestinal disease in a subject in need thereof, comprising administering an effective amount of an inhibitor of KLF11 signaling, thereby treating gastrointestinal disease in the subject.

In certain embodiments, the inhibitor of KLF11 signaling is a small, non-coding RNA molecule.

In certain embodiments, the small, non-coding RNA molecule is selected from the group consisting of an shRNA, an siRNA, and an miRNA.

In certain embodiments, the small, non-coding RNA molecule is an siRNA.

In certain preferred embodiments, the siRNA is encoded by a nucleotide sequence selected from the group consisting of SEQ ID NOs: 1-8 or combinations thereof.

In certain embodiments, the gastrointestinal disease is selected from the group consisting of gastroparesis, functional gastrointestinal disorder, functional gastrointestinal motility disorder and intestinal pseudo obstruction.

In certain embodiments, the functional gastrointestinal disorder is selected from the group consisting of irritable bowel syndrome, functional constipation and unspecified functional bowel disorder.

In another aspect, the invention includes a composition comprising an inhibitor of KLF11 signaling and a pharmaceutically acceptable carrier or adjuvant.

In certain embodiments, the inhibitor of KLF11 signaling is a small, non-coding RNA molecule.

In certain embodiments, the small, non-coding RNA molecule is selected from the group consisting of an shRNA, an siRNA, and an miRNA.

In certain preferred embodiments, the siRNA is encoded by a nucleotide sequence selected from the group consisting of SEQ ID NOs: 1-8 or combinations thereof.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIGS. 1A-1B illustrate the sequences of mouse and human KLF11 siRNAs used in the present invention.

FIGS. 10A-10F demonstrates that siK1fl1 improves GI functions.

DETAILED DESCRIPTION

Definitions

Figure 2:
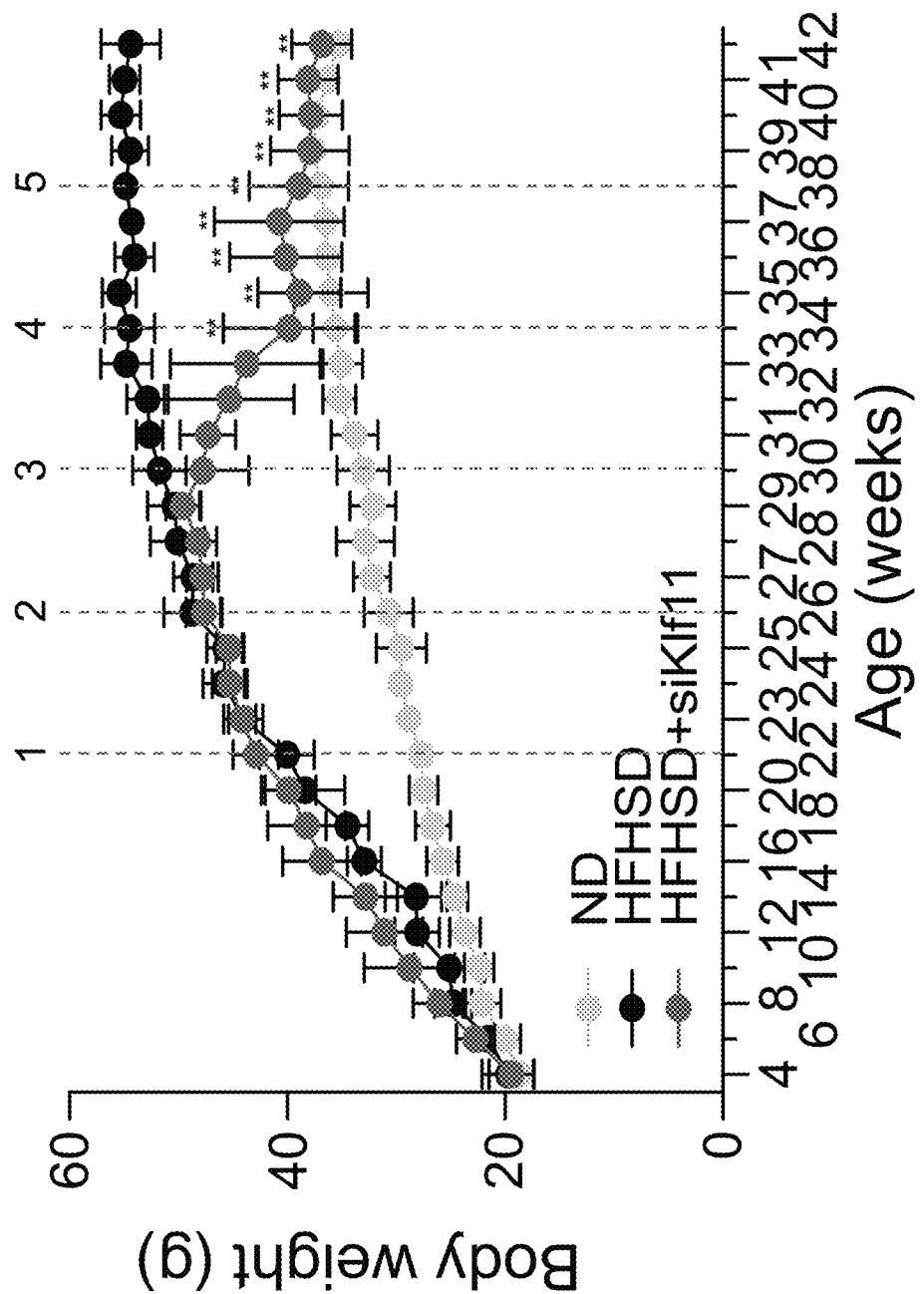
FIG. 2 illustrates that siK1fl1 rescues the obese phenotype in mice fed a HFHSD.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Activation," as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

The term "autoimmune disease" as used herein is defined as a disorder that results from an autoimmune response. An autoimmune disease is the result of an inappropriate and excessive response to a self-antigen. Examples of autoimmune diseases include but are not limited to, Addison's disease, alopecia areata, ankylosing spondylitis, autoimmune hepatitis, autoimmune parotitis, Crohn's disease, diabetes (Type I), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, among others.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. In certain embodiments, the cancer is medullary thyroid carcinoma.

The term "cleavage" refers to the breakage of covalent bonds, such as in the backbone of a nucleic acid molecule.

Cleavage can be initiated by a variety of methods, including, but not limited to, enzymatic or chemical hydrolysis of a phosphodiester bond. Both single-stranded cleavage and double-stranded cleavage are possible. Double-stranded cleavage can occur as a result of two distinct single-stranded cleavage events. DNA cleavage can result in the production of either blunt ends or staggered ends. In certain embodiments, fusion polypeptides may be used for targeting cleaved double-stranded DNA.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody can be replaced with other amino acid residues from the same side chain family and the altered antibody can be tested for the ability to bind antigens using the functional assays described herein.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to, anti-tumor activity as determined by any means suitable in the art.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, the terms "engineered," "genetically engineered," "recombinant," "non-naturally occurring," and "non-natural" are used interchangeably to refer to synthetic polynucleotides and polypeptides that have been intentionally manipulated by humans.

As used herein "endogenous" refers to any material from or produced inside an organism, cell, tissue or system.

As used herein, the term "exogenous" refers to any material introduced from or produced outside an organism, cell, tissue or system.

As used herein, the term "RNA interference" or RNAi is the process by which synthetic small interfering RNAs (siRNAs) or the expression of an RNA molecule, including micro RNAs (miRNAs), short interfering RNAs (siRNAs), or short-hairpin RNAs (shRNAs) cause sequence-specific degradation or translational suppression of complementary endogenous mRNA molecules. As such RNAi is a form of post-transcriptional gene silencing that does not alter the DNA sequence of the target gene.

As used herein, the term "miRNA mimic" refer to double-stranded, synthetic versions of endogenous miRNAs which can resemble or mimic the functions of endogenous miRNA. Synthetic miRNA mimics can be modified (e.g. chemically) to have more or less activity than their endogenous equivalent (e.g. through greater resistance to degradation). In contrast, "miRNA inhibitors" or "antimiRs" refer to synthetic, single-stranded RNA molecules which are able to bind to endogenous target miRNAs and prevent them from regulating their mRNA targets.

The term "expand" as used herein refers to increasing in number, as in an increase in the number of T cells. In one embodiment, the T cells that are expanded ex vivo increase in number relative to the number originally present in the culture. In another embodiment, the T cells that are expanded ex vivo increase in number relative to other cell types in the culture. The term "ex vivo," as used herein, refers to cells that have been removed from a living organism, (e.g., a human) and propagated outside the organism (e.g., in a culture dish, test tube, or bioreactor).

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., sendai viruses, lentiviruses, retroviruses, adenoviruses, and adeno-associated viruses) that incorporate the recombinant polynucleotide.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies can comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

"Fully human" refers to an immunoglobulin, such as an antibody, where the whole molecule is of human origin or consists of an amino acid sequence identical to a human form of the antibody.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

By the term "modified" as used herein, is meant a changed state or structure of a molecule or cell of the invention. Molecules may be modified in many ways, including chemically, structurally, and functionally. Cells may be modified through the introduction of nucleic acids.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

A "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the plasma membrane of a cell.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

A "target site" or "target sequence" refers to a genomic nucleic acid sequence that defines a portion of a nucleic acid to which a binding molecule may specifically bind under conditions sufficient for binding to occur.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The term "transgene" refers to the genetic material that has been or is about to be artificially inserted into the genome of an animal, particularly a mammal and more particularly a mammalian cell of a living animal.

The term "transgenic animal" refers to a non-human animal, usually a mammal, having a non-endogenous (i.e., heterologous) nucleic acid sequence present as an extrachromosomal element in a portion of its cells or stably integrated into its germ line DNA (i.e., in the genomic sequence of most or all of its cells), for example a transgenic mouse. A heterologous nucleic acid is introduced into the germ line of such transgenic animals by genetic manipulation of, for example, embryos or embryonic stem cells of the host animal.

The term "knockout mouse" refers to a mouse that has had an existing gene inactivated (i.e. "knocked out"). In some embodiments, the gene is inactivated by homologous recombination. In some embodiments, the gene is inactivated by replacement or disruption with an artificial nucleic acid sequence.

To "treat" a disease as the term is used herein, means to reduce the frequency or severity of at least one sign or symptom of a disease or disorder experienced by a subject.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, Sendai viral vectors, adenoviral vectors, adeno-associated virus vectors, retroviral vectors, lentiviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention is based on the unexpected discovery that the inhibition of the expression of the gene Kruppel-like factor 11 (KLF11) reduces body fat and weight, restores glucose homeostasis and insulin sensitivity, and improves gastrointestinal (GI) functions in obese diabetic mice. In some embodiments, an inhibitor of KLF11 is a short, non-coding siRNA molecule that prevents the expression of the KLF11 gene by RNA interference. Also provided are methods and compositions for the use of a KLF11-inhibiting siRNA for the treatment of diabetes, obesity, glucose homeostasis dysregulation, and diabetes-related gastrointestinal disorders.

Diabetes and Related Conditions

In one aspect, the invention of the current disclosure provides a method of treating diabetes in a subject in need thereof comprising administering to the subject an effective amount of an inhibitor of KLF11 signaling.

Diabetes or diabetes mellitus refers to a group of diseases that are broadly related to the inability to properly regulate the use of glucose or sugar as the result of defects in the production, secretion, or function of the hormone insulin. Aberrant function of insulin leads to abnormalities of carbohydrate, fat, and protein metabolism. Diabetes is divided into two general types. Type 1, or insulin-dependent diabetes mellitus results from an autoimmune reaction that results in the destruction of insulin-producing β-islet cells in the pancreas, resulting in a systemic lack of insulin. Treatment for the disease consists mainly of regularly monitoring blood glucose levels and injecting insulin several times a day. Failure to control insulin dosage can result in severe hypoglycemia and life-threatening damage to the brain and other functions.

Type 2, or non-insulin-dependent diabetes mellitus (T2DM) is a more complex disease that typically develops in adults and is associated with glucose-responsive tissues such as adipose fat tissue, muscle, and liver that become resistant to the action of insulin. In early stages of T2DM, pancreatic islet cells compensate by secreting excess insulin. Without intervention, β-islet cell dysfunction can result, leading to decompensation and chronic hyperglycemia. Additionally, T2DM may also be accompanied by peripheral insulin resistance, wherein otherwise insulin sensitive cells fail to respond normally. Whereas Type 1 diabetes is often an acute disease that presents early in life, Type 2 diabetes can develop gradually later in life as a result of many factors including genetics and lifestyle. There are several classes of medications commonly used for the treatment of T2DM: 1) insulin release agents that directly stimulate insulin secretion but are at risk of causing hypoglycemia; 2) a diet insulin releaser that enhances glucose-induced insulin secretion but must be taken before each meal; 3) biguanides including metformin that reduce the production of glucose from digestion; 4) insulin sensitizers such as thiazolidinedione derivatives rosiglitazone and pioglitazone which improve peripheral response to insulin by modulating the expression of glucose metabolic genes, but has side effects such as weight gain, edema and hepatotoxicity; 5) insulin injection, often required in late-stage T2DM.

The metabolic nature of type 2 diabetes and the abnormally high blood sugar that results from the condition often leads to the development of symptoms and disorders that affect a wide range of body tissues. Diabetes is linked to higher incidences of obesity, fatty liver disease, hyperlipidemia, fatty liver disease, and GI motility disorders including gastroparesis and constipation.

T2DM-related insulin resistance is generally associated with atherosclerosis, obesity, hyperlipidemia and essential hypertension. This group of abnormal conditions constitutes "metabolism" or insulin resistance. In addition, insulin resistance is associated with fatty liver disease, which may lead to chronic inflammation or nonalcoholic steatohepatitis, fibrosis and cirrhosis. Nonalcoholic fatty liver disease begins with the accumulation of triacylglycerol in the liver and is defined as the presence of cytoplasmic lipid droplets in more than 5% of hepatocytes or TAG levels exceeding the 95th percentile for healthy individuals. Both T2DM and fatty liver disease share comorbidities and adversely impact the progression of each disease. Type 2 diabetes is a risk factor for progressive liver disease and liver-related death in patients with fatty liver disease, whereas fatty liver disease may be a marker of cardiovascular risk and mortality in individuals with Type 2 diabetes. Nonalcoholic steatohepatitis, a histological subtype of NAFLD characterized by hepatocyte injury and inflammation, is present in approximately 10% of patients with T2DM and is associated with an increased risk for the development of cirrhosis and liver-related death.

Diabetic gastroparesis, which is a common, yet serious, chronic disorder of the upper gastrointestinal tract, is defined by the presence of delayed gastric emptying in the absence of physical obstruction and is associated with symptoms such as nausea, vomiting, early satiation, bloating, and abdominal pain. Currently, the only FDA-approved drug for diabetic gastroparesis is metoclopramide, a dopamine D2 receptor antagonist and 5-HT3 receptor antagonist with weak 5-HT4 agonist activity, which is indicated for the relief of symptoms associated with acute and recurrent diabetic gastric stasis for no longer than 12 weeks of treatment. However, metoclopramide treatment is associated with significant side effects such as sudden muscle spasms and depression/mood changes.

Gene Expression Regulation by RNA Interference of KLF11 Signaling

In one aspect, the invention provides method of using an interfering RNA molecule to inhibit KLF11 signaling in order to treat diabetes and conditions related to diabetes. In certain embodiments, the KLF11 signaling inhibitor is a small, non-coding RNA molecule that regulates KLF11 activity through RNA interference.

RNA interference (RNAi) is a sequence-specific RNA targeting process that provides a direct way to knockdown and effectively silence any gene containing a homologous sequence. The mechanism of gene regulation by RNAi involves the expression of non-coding, silencing RNA molecules that are complementary to the mRNA molecules transcribed from the target gene. The complementary RNA molecules are expressed as long, double-stranded RNA (dsRNA) that are then cleaved by an RNase III/helicase protein, Dicer, into small interfering RNA (siRNA) molecules of 19-27 nucleotides (nt) with 2-nt overhangs at the 3' ends. Afterwards, the siRNAs are incorporated into a ribonuclease protein complex called the RNA-induced-silencing-complex (RISC). One strand of siRNA remains associated with RISC to guide the complex towards complementary target RNA. This siRNA-directed endonuclease digests the target mRNA, resulting in truncation and inactivation of the targeted RNA. Degradation of targeted mRNA results in decreased translation of the resulting protein. In this way, siRNA-directed RNAi is able effectively silence or knock-out a targeted gene without mutating or altering the genomic DNA sequence.

miRNAs are small, non-coding RNA molecules that are typically 20-22 nucleotides in length. miRNAs act as key regulators of gene expression and function which act to modify gene expression by interacting with post-transcription RNA and modulating its stability and subsequent translation. Understanding of the biological roles of ncRNAs, including miRNAs is advancing rapidly. Numerous evolutionary studies have revealed that non-coding RNAs could be expressed in nearly 4-fold greater quantity than protein-coding RNAs.

Endogenous miRNAs are transcribed as 100-1000 nucleotide (nt) primary miRNAs (pri-RNAs) by RNA polymerase II. miRNAs may be modified by 5' capping and 3' poly(A) tailing. The miRNA-encoding portion of the pri-miRNA forms a hairpin, which is cleaved by the dsRNA-specific ribonuclease Drosha and its cofactor DiGeorge syndrome critical region 8 (DGCR8), to form a pre-miRNA that is about 60-70 nt long. The pre-miRNA is further processed by Dicer and the trans-activator RNA-binding protein TRBP to yield a miRNA duplex containing two mature miRNAs (5'- and 3'-strand miRNAs). Each mature miRNA is about 22-23 nt in length.

Depending on the degree of complementarity between the mature miRNA and its target, several mechanisms of mRNA silencing can occur. The leading bases from positions 2 to 7 of the mature miRNA are termed the 'seed' sequence and provide most of the pairing specificity with the target mRNA. In some cases, complete pairing between the seed sequence and its cognate target is sufficient to mediate cleavage and degradation of the cognate mRNA. More typically for mammalian and viral mRNA targets, however, cleavage is impaired by mismatched pairing in the seed and other regions and translational inhibition occurs through physical interference with the binding of translational machinery. Since the complementary length of seed sequence required for miRNAs to target cognate mRNAs is short, each miRNA has the possibility to target and modulate hundreds of transcripts. Furthermore, mRNA molecules can, in turn, also be acted upon by numerous distinct miRNAs. While most miRNAs decrease target protein levels by less than 2-fold, this is often sufficient to exert a significant physiological effect. Thus, the endogenous miRNA pathway represents a highly efficient system to simultaneously fine-tune the expression of numerous genes as well as modulate specific functional pathways. miRNAs are predicted to control the activity of approximately 30% of all protein-coding genes in mammals, and play important roles in normal physiological processes ranging from embryonic development to hematopoietic cell development to diseases ranging from cardiovascular disease, cancer, and immune disorders.

KLF11 Targeting siRNAs

In some embodiments of the invention, the inhibitor of KLF11 signaling is an interfering RNA molecule. In some embodiments, the interfering RNA molecule is a short interfering RNA or siRNA.

The sequence of selected KLF11-targeting siRNA molecules is listed in Table 1

TABLE 1

| SEQ ID NO: | Name: | Sequence: | |
|---|---|---|---|
| 1. | Mouse | siKlf11-1 sense | GUUCCUUCCC AAGUAGUUAUU |
| 2. | Mouse | siKLF11-1 antisense | GACAAGGAAGG GUUCAUCAAU |
| 3. | Mouse | siKLF11-2 sense | UCUGAUUUCUG UCCCUGUAUU |
| 4. | Mouse | siKLF11-2 antisense | GGAGACUAAAG ACAGGGACAU |
| 5. | Human | siKLF11-1 sense | ACAGUUUACU CAGCACUAAUU |
| 6. | Human | siKLF11-1 antisense | CCUGUCAAAUG AGUCGUGAUU |
| 7. | Human | siKLF11-2 sense | CACCUGAACUA CCAAAAGAUU |
| 8. | Human | siKLF11-2 antisense | GTGUGGACUUG AUGGUUUUCU |

Methods of Treatment

Also provided is a method of treating diabetes in a subject in need thereof. The method comprises administering to the subject an effective amount of an inhibitor of KLF11 signaling. In some embodiments, the inhibitor of KLF11 signaling is a small, non-coding RNA molecule. In some embodiments, the small, non-coding RNA molecule is selected from the group comprising an shRNA, an siRNA, and a miRNA. In some embodiments, the small, non-coding RNA molecule is an siRNA. In some embodiments, the KLF11-targeting siRNA molecules are those listed in Table 1.

In some embodiments, the inhibitor of KLF11 signaling further comprises a pharmaceutically acceptable carrier or adjuvant.

Also provided is a composition comprising an inhibitor of KLF11 signaling as disclosed herein and a pharmaceutically acceptable carrier or adjuvant. In some embodiments, the inhibitor of KLF11 signaling is a small, non-coding RNA molecule. In some embodiments, the small, non-coding RNA molecule is selected from the group comprising an shRNA, an siRNA, and a miRNA. In some embodiments, the small, non-coding RNA molecule is an siRNA. In some embodiments, the KLF11-targeting siRNA molecules are those listed in Table 1.

Also provided is a method for treating gastrointestinal disease comprising administering an effective amount of an inhibitor of KLF11 signaling to a subject in need thereof, thereby treating gastrointestinal disease in the subject. In some embodiments, the inhibitor of KLF11 signaling is a small, non-coding RNA molecule. In some embodiments, the small, non-coding RNA molecule is selected from the group comprising an shRNA, an siRNA, and a miRNA. In some embodiments, the small, non-coding RNA molecule is an siRNA. In some embodiments, the KLF11-targeting siRNA molecules are those listed in Table 1.

In some embodiments, the gastrointestinal disease is selected from the group consisting of gastroparesis, functional gastrointestinal disorder, functional gastrointestinal motility disorder and intestinal pseudo obstruction. In further embodiments, the functional gastrointestinal disorder is selected from the group consisting of irritable bowel syndrome, functional constipation and unspecified functional bowel disorder.

Provided is a method for reducing body weight comprising administering an effective amount of an inhibitor of KLF11 signaling to a subject in need thereof, thereby reducing body weight in the subject. In some embodiments, the inhibitor of KLF11 signaling is a small, non-coding RNA molecule. In some embodiments, the small, non-coding RNA molecule is selected from the group comprising an shRNA, an siRNA, and a miRNA. In some embodiments, the small, non-coding RNA molecule is an siRNA. In some embodiments, the KLF11-targeting siRNA molecules are those listed in Table 1.

Also provided is a method for reducing blood glucose comprising administering an effective amount of an inhibitor of KLF11 signaling to a subject in need thereof, thereby lowering blood glucose in the subject. In some embodiments, the inhibitor of KLF11 signaling is a small, non-coding RNA molecule. In some embodiments, the small, non-coding RNA molecule is selected from the group comprising an shRNA, an siRNA, and a miRNA. In some embodiments, the small, non-coding RNA molecule is an siRNA. In some embodiments, the KLF11-targeting siRNA molecules are those listed in Table 1.

Also provided is a method for increasing insulin sensitivity comprising administering an effective amount of a inhibitor of KLF11 signaling to a subject in need thereof, thereby increasing insulin sensitivity in the subject. In further embodiments, administration of the inhibitor of KLF11 signaling results in a decrease in blood glucose levels in the subject. In some embodiments, the inhibitor of KLF11 signaling is a small, non-coding RNA molecule. In some embodiments, the small, non-coding RNA molecule is selected from the group comprising an shRNA, an siRNA, and a miRNA. In some embodiments, the small, non-coding RNA molecule is an siRNA. In some embodiments, the KLF11-targeting siRNA molecules are those listed in Table 1.

In some untreated diabetic subjects, insulin is not produced or is only produced at low levels in the beta cells of the subject. In untreated diabetic subjects, there is a reduction of beta cells located in islet cells. Islet cells are located in the pancreas of the subject.

Also provided is a method for treating diabetes comprising administering an effective amount of an inhibitor of KLF11 signaling to a subject in need thereof, thereby treating diabetes in the subject. In some embodiments, the diabetes is type 1 or type 2 diabetes. In some embodiments, administration of the inhibitor of KLF11 signaling results in a decrease in blood glucose levels in the subject. In some embodiments, the inhibitor of KLF11 signaling is a small, non-coding RNA molecule. In some embodiments, the small, non-coding RNA molecule is selected from the group comprising an shRNA, an siRNA, and a miRNA. In some embodiments, the small, non-coding RNA molecule is an siRNA. In some embodiments, the KLF11-targeting siRNA molecules are those listed in Table 1.

In some embodiments of any one of the previous methods, the inhibitor of KLF11 signaling is administered by injection. In some embodiments, the inhibitor of KLF11 signaling may be administered orally, parenterally, subcutaneously, intravenously, intramuscularly, intraperitoneally, by nasal instillation, by implantation, by intracavitary or intravesical instillation, intraocularly, intraarterially, intralesionally, transdermally, or by the application to mucous membranes.

In some embodiments of any one of the previous methods, the inhibitor of KLF11 signaling further comprises a pharmaceutically acceptable carrier or adjuvant.

It is envisaged that the inhibitor of KLF11 signaling may be administered to a subject in combination with other suitable treatments for diabetes (type 1 or type 2). In some embodiments, the other treatments are insulin, insulin sensitizers (Thiazolidinedione), metformin, glucagon like peptide-1 (GLP-1) receptor agonists (Exenatide, Albiglutide, Dulaglutide, Liraglutide, Lixisenatide), dipeptidylpeptidase-4 (DPP4) inhibitors (Sitagliptin, Vildagliptin, Alogliptin, Linagliptin), sodium-glucose transporters-2 (SGLT2) inhibitors (Dapagliflozin, Empagliflozin), and sulfonylureas (Glimepiride).

It is envisaged that the inhibitor of KLF11 signaling may be administered to a subject in combination with other suitable treatments for a gastrointestinal disorder. In some embodiments, the other treatments are prokinetics, 5-HT4 receptor agonist (Prucalopride, tegaserod and Velusetrag), ghrelin agonist (Relamorelin), dopamine receptor antagonists and 5-HT4 agonists (metoclopramide and domperidone), motilin receptor agonists (Macrolide antibiotics: Erythromycin and azithromycin)], anti-emetic agents (Aprepitant, Promethazine, Prochlorperazine, and Ondansetron), and agents acting on secretion (Lubiprostone and Tenapanor).

In some embodiments, the KLF11 inhibiting siRNA comprises a nucleic acid sequence comprising SEQ ID NOs: 1-8 or combinations thereof.

Polynucleotide Delivery Systems

Polynucleotide-based treatments, such as those described in the present invention, depend upon a vector or vector system to shuttle the genetic constructs into target cells. Methods of introducing a nucleic acid into tumor or tissue cells include physical, biological and chemical methods. Physical methods for introducing one or several polynucleotides, such as RNA or anti-sense oligonucleotides, into host cells or tissues include calcium phosphate precipitation, lipofection, particle bombardment, microinjection, electroporation, and the like. Polynucleotides can be introduced into target cells using commercially available methods which include electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany). Oligonucleotides can also be introduced into cells using cationic liposome mediated transfection using lipofection, using polymer encapsulation, using peptide mediated transfection, or using biolistic particle delivery systems such as "gene guns" (see, for example, Nishikawa, et al. Hum Gene Ther., 12(8):861-70 (2001).

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes.

An exemplary colloidal system for use as a delivery vehicle in vitro and in vivo is a liposome (e.g., an artificial membrane vesicle).

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Choi") can be obtained from Calbiochem-Behring; dimyristyl phosphatidylglycerol ("DMPG") and other lipids may be obtained from Avanti Polar Lipids, Inc. (Birmingham, AL). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., (1991) *Glycobiology* 5: 505-10). However, compositions that have different structures in solution than the normal vesicular structure are also encompassed. For example, the lipids may assume a micellar structure or merely exist as non-uniform aggregates of lipid molecules. Also contemplated are lipofectamine-nucleic acid complexes. In some embodiments of the current invention, oligonucleotides can be delivered using lipid or chemical systems such as e.g., a nanoparticle, a dendrimer, a polymer, liposomal, or a cationic delivery system.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362. Currently, the most efficient and effective way to accomplish the transfer of genetic constructs into living cells is through the use of vector systems based on viruses that have been made replication-defective. Some of the most effective vectors known in the art are those based on adeno-associated viruses (AAVs). AAVs are small viruses of the parvoviridae family that make attractive vectors for gene transfer in that they are replication defective, not known to cause any human disease, cause only a very mild immune response, can infect both actively dividing and quiescent cells, and stably persist in an extrachromosomal state without integrating into the target cell's genome. In certain embodiments, the pre-RNA splicing agents of the invention can be delivered to a subject via an AAV-based system.

Regardless of the method used to introduce the nucleic acid into the cell, a variety of assays may be performed to confirm the presence of the nucleic acid in the cell. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Pharmaceutical Compositions

Provided is a composition comprising an inhibitor of KLF11 signaling. In some embodiments, the inhibitor of KLF11 signaling is a small, non-coding RNA molecule. In some embodiments, the small, non-coding RNA molecule is selected from the group consisting of an shRNA, an siRNA, and an miRNA.

In some embodiments, the small, non-coding RNA molecule is an siRNA comprising a nucleic acid sequence comprising SEQ ID NO: 1, 2, 3, 4, 5, 6, 7, 8 or combinations thereof.

Pharmaceutical compositions of the present invention may comprise an inhibitor of KLF11 signaling as described herein, in combination with one or more pharmaceutically or physiologically acceptable carriers, diluents, adjuvants or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

Pharmaceutical compositions of the present invention may be administered in solid or liquid form such as tablets, capsules, powders, solutions, suspensions, emulsions and the like. Pharmaceutical compositions of the present invention may be administered orally, parenterally, subcutaneously, intravenously, intramuscularly, intraperitoneally, by nasal instillation, by implantation, by intracavitary or intravesical instillation, intraocularly, intraarterially, intralesionally, transdermally, or by the application to mucous membranes. In some embodiments, the composition may be applied to the nose, throat or bronchial tubes, for example by inhalation.

The dosage of the above treatments to be administered to a patient will vary with the precise nature of the condition being treated and the recipient of the treatment and can be determined by physical and physiological factors such as body weight, severity of condition, previous or concurrent therapeutic interventions, and on the route of administration. The scaling of dosages for human administration can be performed according to art-accepted practices. The dose for a miR mimic, for example, will generally be in the range 1 to about 100 mg for an adult patient, usually administered monthly for a period between 1 and 12 months. The preferred monthly dose is 1 to 10 mg per month although in some instances larger doses of over 10 mg per month may be used.

Human dosage amounts can initially be determined by extrapolating from the amount of compound used in mice, as a skilled artisan recognizes it is routine in the art to modify the dosage for humans compared to animal models. In certain embodiments it is envisioned that the dosage may include an effective amount from between about 1 microgram/kg/body weight, from 5 microgram/kg/body weight, 10 microgram/kg/body weight, 50 microgram/kg/body weight, 100 microgram/kg/body weight, 200 microgram/kg/body weight, 350 microgram/kg/body weight, 500 microgram/kg/body weight, 1 milligram/kg/body weight, 5 milligram/kg/body weight, 10 milligram/kg/body weight, 50 milligram/kg/body weight, 100 milligram/kg/body weight, 200 milligram/kg/body weight, 350 milligram/kg/body weight, or 500 milligram/kg/body weight, to 1000 mg/kg/body weight or more per administration, and any range derivable therein. In other embodiments, the effective amount may be about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, or about 100 mg/Kg body weight. In other embodiments, it is envisaged that effective amounts may be in the range of about 1 micrograms compound to about 100 mg compound. In other embodiments, the effective amount may be about 1, 2, 3, 4, 5, 6, 7, 8, 9, 10, 11, 12, 13, 14, 15, 16, 17, 18, 19, or 20 mg per single dose. In another embodiment, the effective amount comprises less than about 2, 3, 4, 5, 6, 7, 8, 9, 10, 15, 20, 25, 30, 35, 40, 45, 50, 55, 60, 65, 70, 75, 80, 85, 90, 95 mg daily. In an exemplary embodiment, the effective amount comprises less than about 50 mg daily. Of course, the single dosage amount or daily dosage amount may be adjusted upward or downward, as is routinely done in such treatment protocols, depending on the results of the initial clinical trials and the needs of a particular subject. Those of skill in the art would recognize the conditions and situations warranting modified dosing.

The precise determination of what would be considered an effective dose is based on factors individual to each subject, including their size, age, sex, weight, and condition of the particular subject. Dosages can be readily ascertained by those skilled in the art from this disclosure and the knowledge in the art.

Optionally, the methods of the invention provide for the administration of a composition of the invention to a suitable animal model to identify the dosage of the composition(s), concentration of components therein and timing of administering the composition(s), which elicit tissue repair, reduce cell death, or induce another desirable biological response. Such determinations do not require undue experimentation, but are routine and can be ascertained without undue experimentation.

The biologically active agents can be conveniently provided to a subject as sterile liquid preparations, e.g., isotonic aqueous solutions, suspensions, emulsions, dispersions, or viscous compositions, which may be buffered to a selected pH. Cells and agents of the invention may be provided as liquid or viscous formulations. For some applications, liquid formations are desirable because they are convenient to administer, especially by injection. Where prolonged contact with a tissue is desired, a viscous composition may be preferred. Such compositions are formulated within the appropriate viscosity range. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof.

Sterile injectable solutions are prepared by suspending talampanel and/or perampanel in the required amount of the appropriate solvent with various amounts of the other ingredients, as desired. Such compositions may be in admixture with a suitable carrier, diluent, or excipient, such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the cells or agents present in their conditioned media.

The compositions can be isotonic, i.e., they can have the same osmotic pressure as blood and lacrimal fluid. The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions, if desired, can be maintained at the selected level using a pharmaceutically acceptable thickening agent, such as methylcellulose. Other suitable thickening agents include, for example, xanthan gum, carboxymethyl cellulose, hydroxypropyl cellulose, carbomer, and the like. The choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form). Those skilled in the art will recognize that the components of the compositions should be selected to be chemically inert.

It should be understood that the method and compositions that would be useful in the present invention are not limited to the particular formulations set forth in the examples. The following examples are put forth so as to provide those of ordinary skill in the art with a complete disclosure and description of how to make and use the cells, expansion and culture methods, and therapeutic methods of the invention, and are not intended to limit the scope of what the inventor regard as his invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting", (Babar, 2011); "Current Protocols in Immunology" (Coligan, 2002). These techniques are applicable to the production of the polynucleotides and polypeptides of the invention, and, as such, may be considered in making and practicing the invention. Particularly useful techniques for particular embodiments will be discussed in the sections that follow.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Inhibition of KLF11 Expression by RNA Interference

A series of siRNA molecules were designed to target KLF11 mRNA transcribed from both mouse and human KLF11 genes. (FIG. 1A) The sequence and structure of the mouse Klf11 siRNAs (siKlf11-1 and siKlf11-2, ThemoFisher Scientific). siKlf11-1 and siKlf11-2 are complementary to mouse Klf11 mRNA (503-521 and 946-964, respectively in NM 178357.3). (FIG. 1B) The sequence and structure of the human KLF11 siRNAs (siKLF11-1 and siKLF11-2, Fisher Scientific). siKLF11-1 and siKLF11-2 are complementary to mouse KLF11 mRNA (434-452 and 824-842, respectively in NM 003597.4).

Example 2: Treatment of Obesity-Related Diabetes by Inhibition of KLF11 Expression Studies were then undertaken to determine whether treatment with siK1f11 rescues the obese phenotype that develops in mice fed a diet high in sucrose and fructose. (FIG. 2) Male C57 mice were fed a high-fat high-sucrose diet (HFHSD) for 18 weeks (4-22 weeks of age) and subsequently injected at 22, 26, 30, 34 and 38 weeks (5 injections total) with either the siK1f11 mix (siK1f11-1 and siK1f11-2) or no injection over a 20-week period (22-42 weeks of age), mice were fed with either a HFHSD or a normal diet (ND). Body weight was measured weekly post-injection (PI). n=6 per group. **p<0.01 (siK1f11 versus no injection in HFHSD fed mice). The siK1f11 mix was used for injection throughout subsequent studies in this disclosure.

Figure 3:
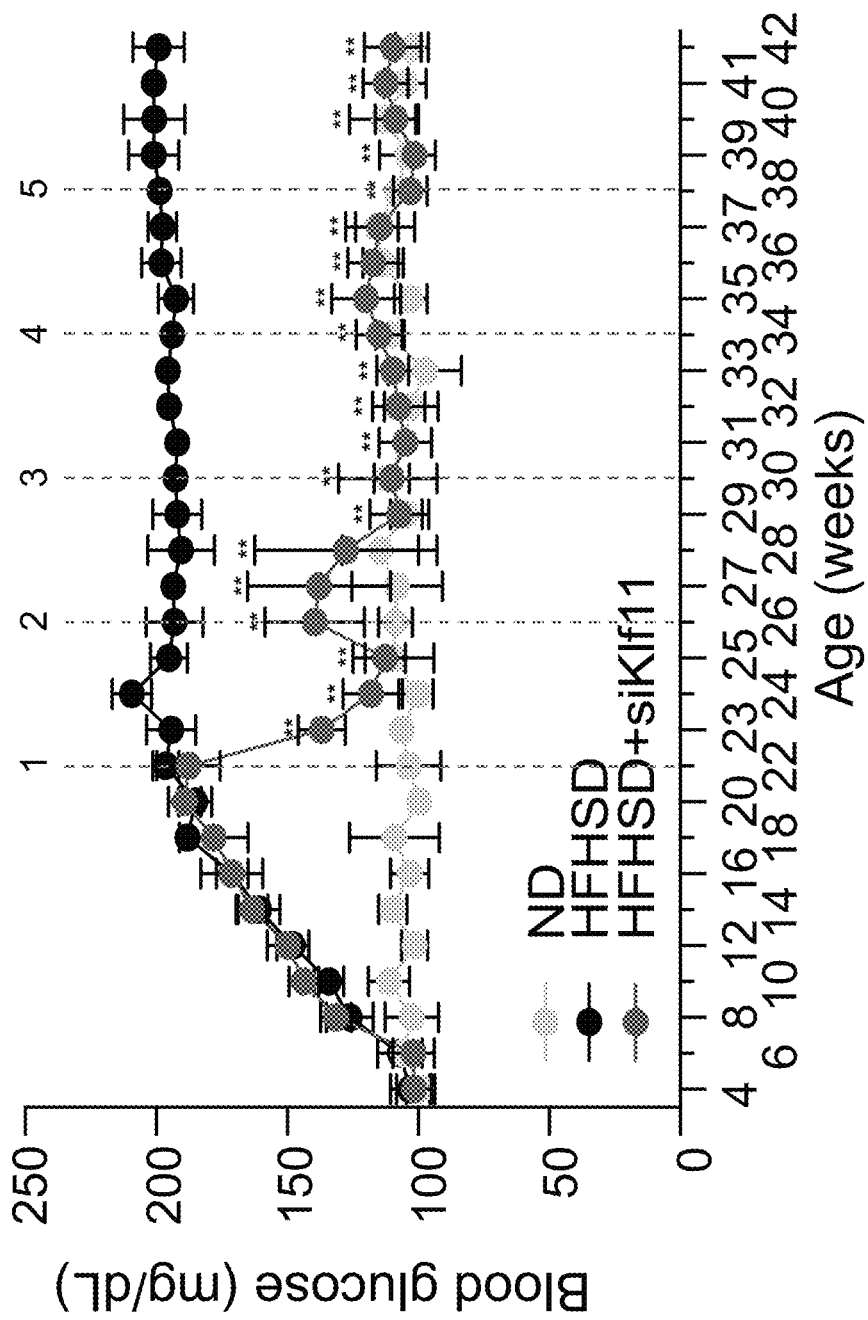
FIG. 3 illustrates that siK1fl1 rescues the diabetic phenotype in mice fed a HFHSD.
Figure 4B:
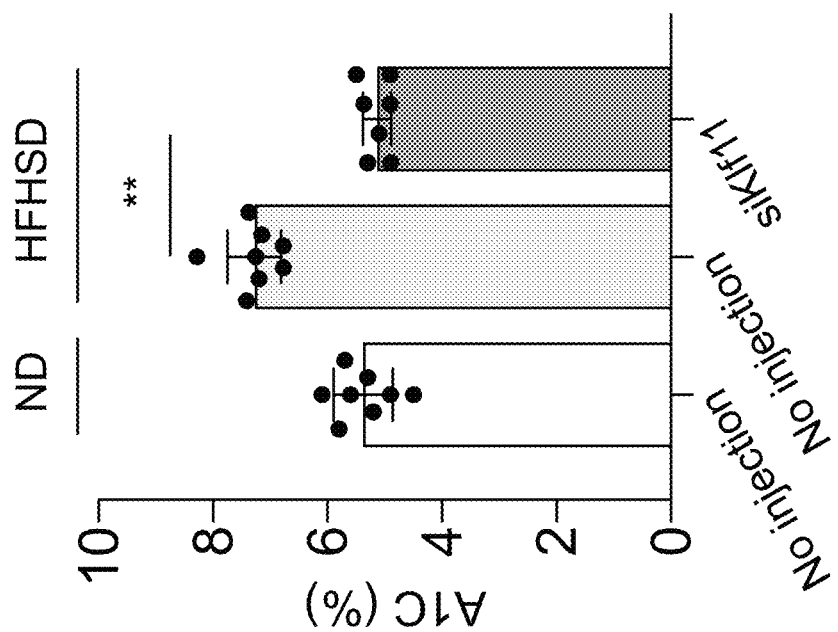
FIGS. 4A-4B illustrate that siK1fl1 lowers glucose levels by restoring basal insulin levels and decreasing A1C levels in HFHSD-induced diabetic mice.
Figure 4A:
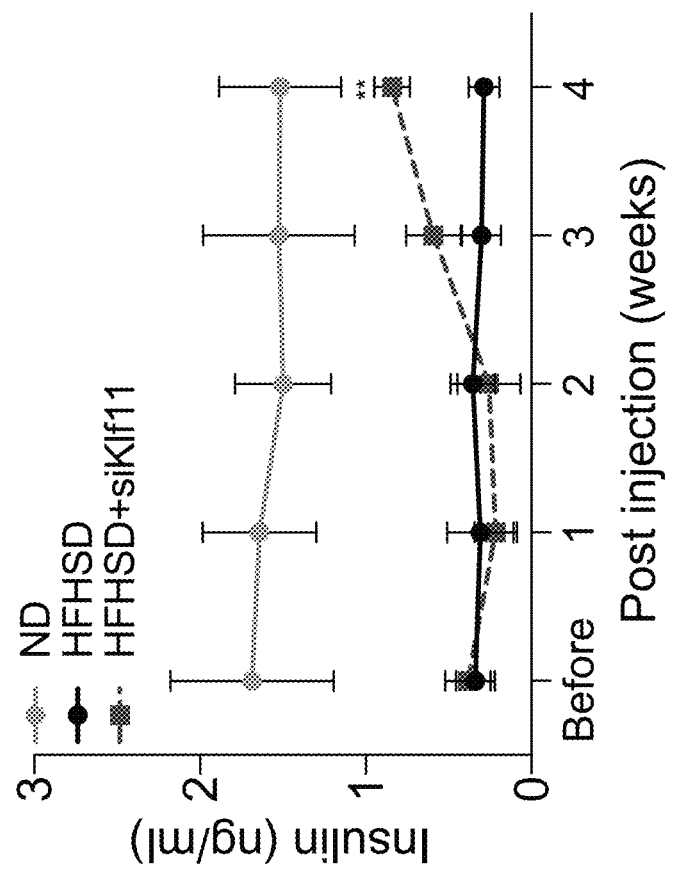

The ability of siK1f11 treatment to rescue the diabetic phenotype in mice fed a HFHSD was then determined. (FIG. 3) Fasting blood glucose was measured weekly in mice from FIG. 2. n=6 per group. p<0.01 (siK1f11 versus no injection in HFHSD fed mice). siK1f11 was further observed to lower glucose levels by restoring basal insulin levels in HFHSD-induced diabetic mice. (FIG. 4A) Insulin was measured each week in male C57 mice fed a ND or a HFHSD for 4 weeks PI with either the siK1f11 or given no injection. (FIG. 4B) A1C was measured at 4 weeks PI. n=8 per condition for each experiment. p<0.01 (siK1f11 versus no injection in HFHSD fed mice).

Figure 5:
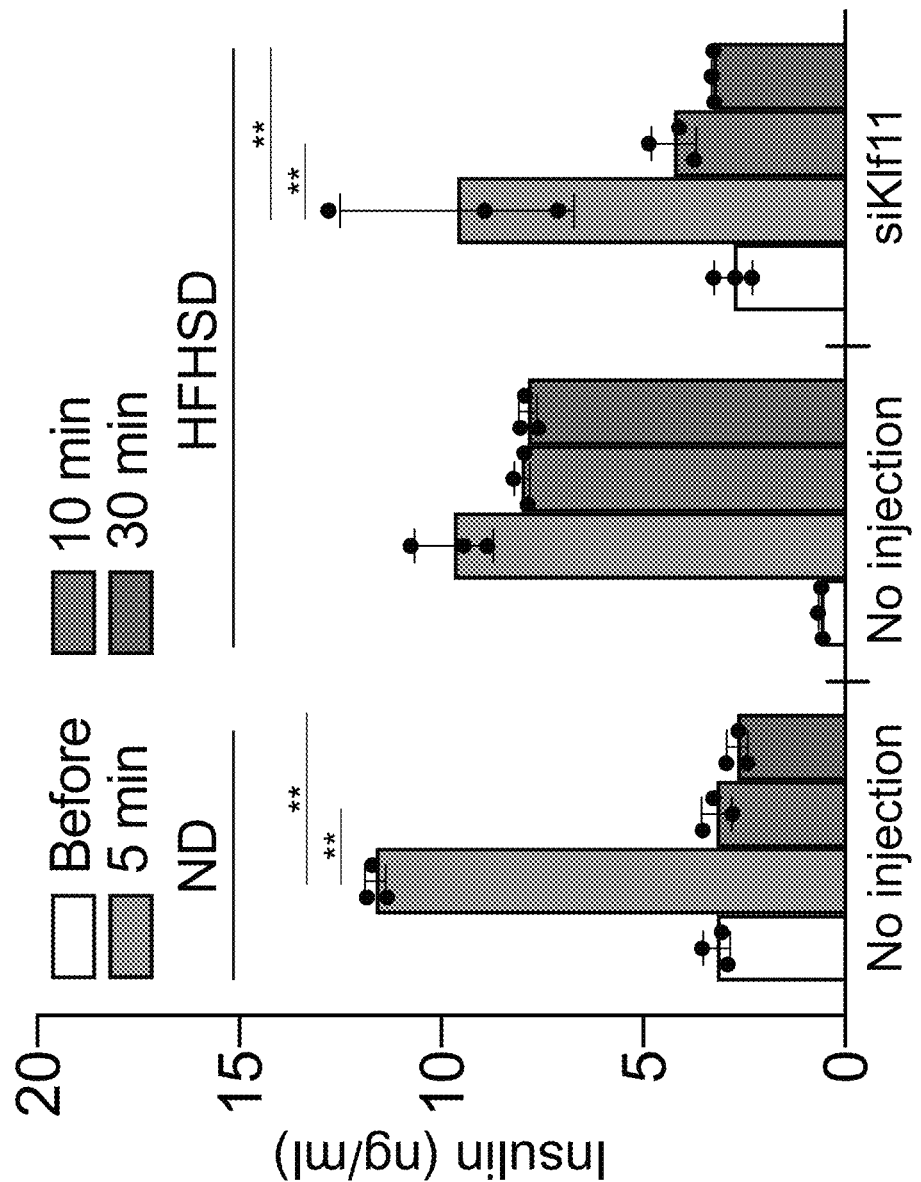
FIG. 5 illustrates siK1fl1 restoring post-prandial insulin sensitivity in HFHSD-induced diabetic mice.
Figure 6:
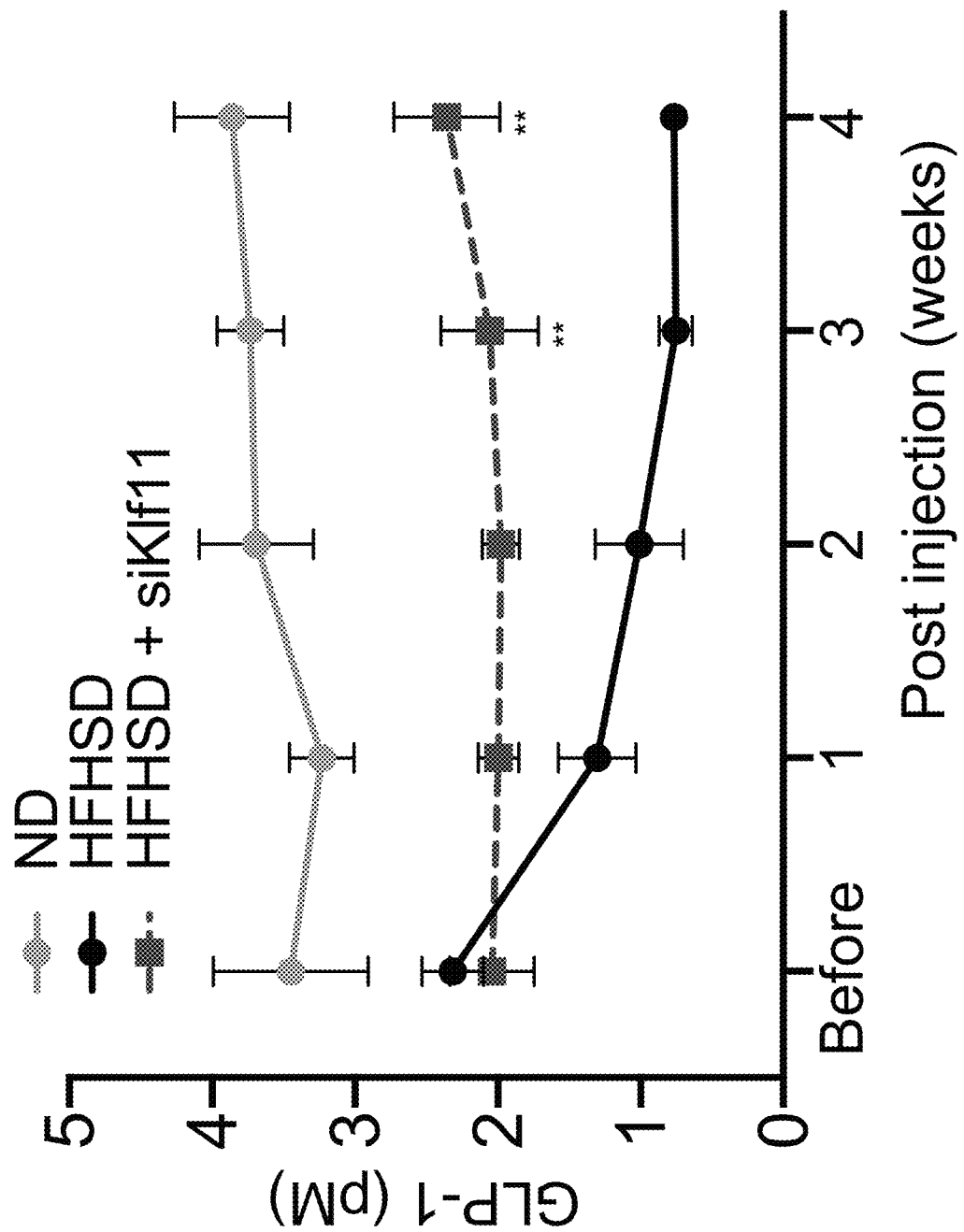
FIG. 6 illustrates that siK1fl1 prevents the loss of GLP-1 in HFHSD-induced diabetic mice.
Figure 7:
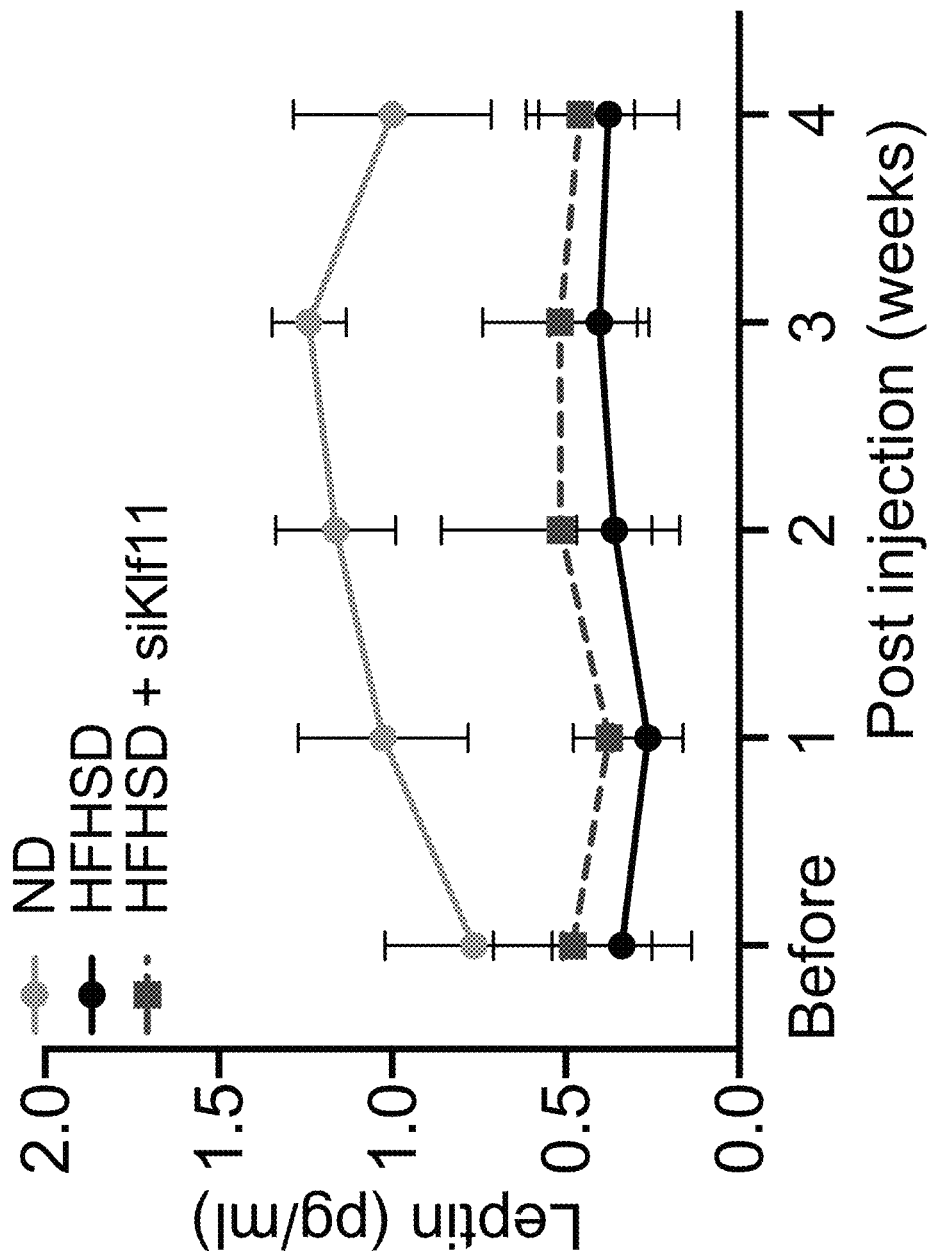
FIG. 7 depicts that siK1fl1 maintains leptin levels in HFHSD-induced diabetic mice.

Follow-up studies were then conducted to observe whether inhibition of KLF11 signaling by siK1f11 restores prandial insulin sensitivity in HFHSD-induced diabetic mice. (FIG. 5) Insulin was measured before and at 5 min, 10 min, and 30 min after an injection of glucose into male C57 mice fed a ND or a HFHSD for 4 weeks PI with either the siK1f11 or given no injection. n=3 per condition for each experiment. p<0.01, (10 and 30 minutes versus 5 minutes). Similarly, siK1f11 was further observed to prevent the loss of GLP-1 in HFHSD-induced diabetic mice (FIG. 6). GLP-1 levels were measured weekly in male C57 mice fed a ND or a HFHSD for 4 weeks PI with either siK1f11 or given no injection. n=7 per condition for each experiment. <0.01 (siK1f11 versus no injection in HFHSD fed mice). At the same time, the ability of siK1f11 to maintain leptin levels in HFHSD-induced diabetic mice was observed (FIG. 7). Leptin levels were measured weekly in male C57 mice fed a ND or a HFHSD for 4 weeks PI with either siK1f11 or given no injection. n=7 per condition for each experiment.

Example 3: Restoring Blood Sugar Regulation by KLF11 Inhibition

Figure 8B:
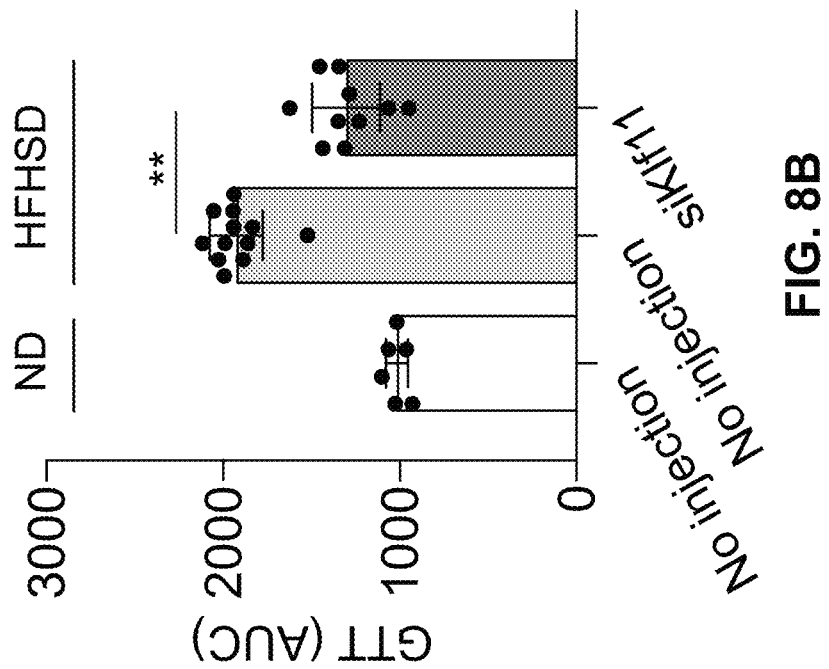
FIGS. 8A-8B depicts that siK1fl1 significantly improves glucose tolerance in HFHSD-induced diabetic mice.
Figure 8A:
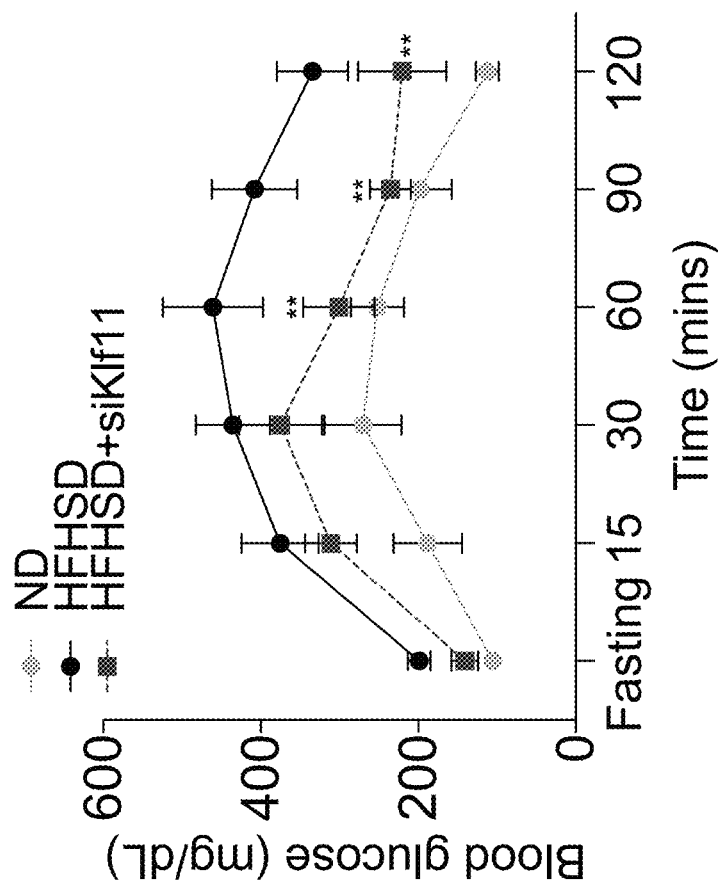
Figure 9B:
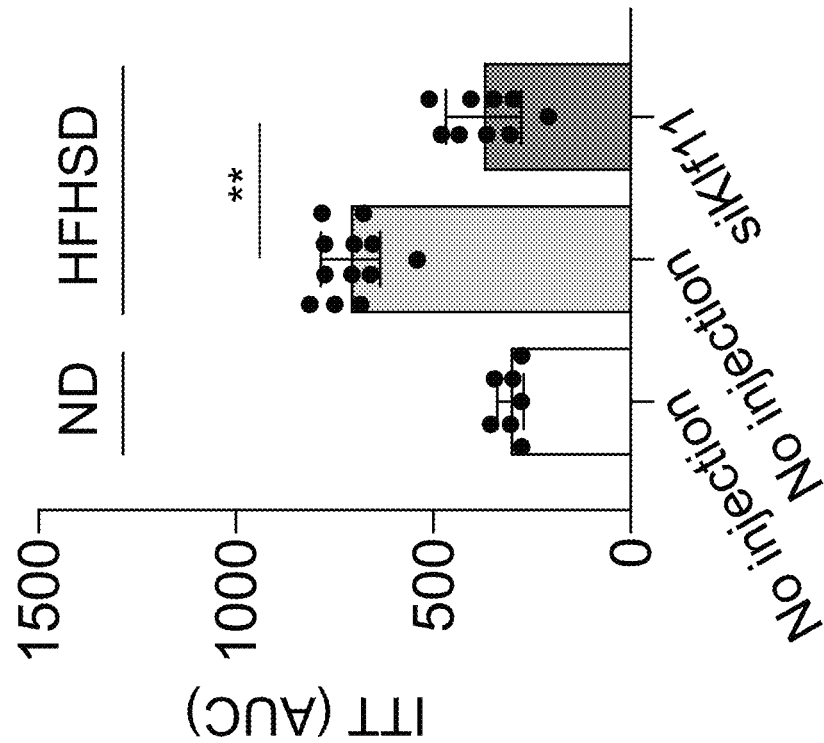
FIGS. 9A-9B depicts that siK1fl1 significantly improves insulin tolerance in HFHSD-induced diabetic mice.
Figure 9A:
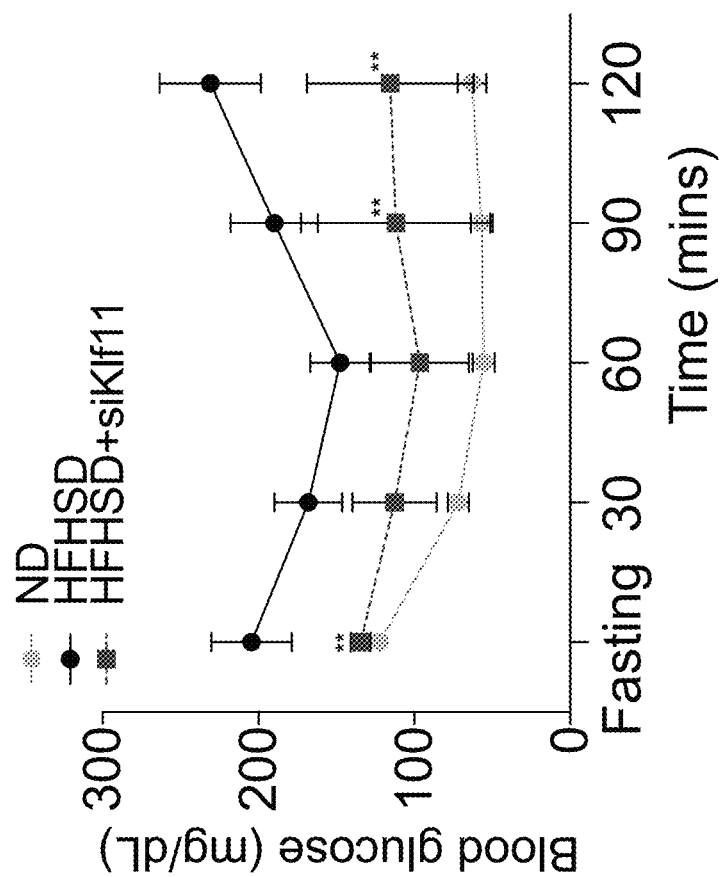

A series of studies was then conducted to observe whether treatment with siK1f11 was able to significantly improve glucose tolerance in HFHSD-induced diabetic mice. (FIGS. 8A and 8B) Glucose tolerance test (GTT) and area under the curve (AUC) was determined in male C57 mice fed a ND or a HFHSD over 4 weeks PI with either the siK1f11 or given no injection. n=6-12 per condition for each experiment. p<0.01, (siK1f11 versus no injection in HFHSD fed mice). Likewise, siK1f11 significantly improved insulin tolerance in HFHSD-induced diabetic mice. (FIGS. 9A and 9B) Insulin tolerance test (ITT) and area under the curve (AUC) in male C57 mice fed a ND or a HFHSD for 4 weeks PI with either the siK1f11 or given no injection. n=7-12 per condition for each experiment. p<0.01, (siK1f11 versus no injection in HFHSD fed mice). Without wishing to be bound by theory, these data suggested knock-down of KLF11 signaling is able to restore normal levels of glucose and insulin tolerance in obese-diabetic mice.

Example 4: Improving Gastrointestinal Function by KLF11 Inhibition

Figure 15:
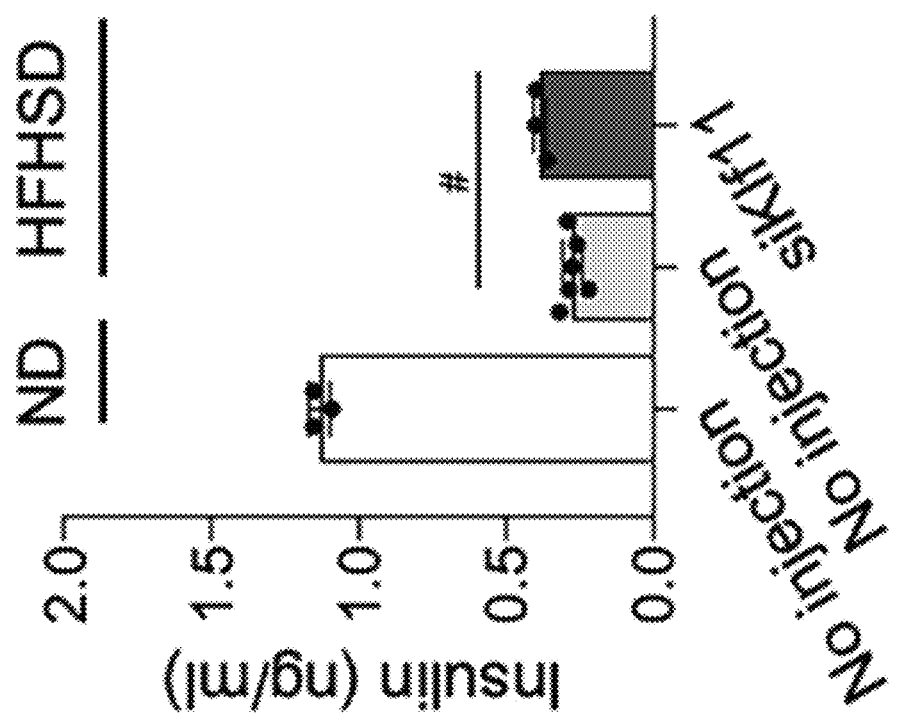
FIG. 15 illustrates insulin levels in mice fed an HFHSD (diabetic) with either treatment with siK1fl1 or given no injection at 4 weeks PI.

Defects in gastrointestinal function are frequent complications associated with obesity and diabetes. Follow-up studies with siK1f11 observed whether KLF11 inhibition could also improve GI function in affected mice, along with the established improvements in body weight and blood sugar homeostasis. (FIG. 10A) Total GI transit time, (FIG. 10B) fecal pellet output, and (FIG. 10C) colonic transit time in male C57 mice fed a ND or a HFHSD measured 4 weeks PI with either the siK1f11 or given no injection. (FIG. 10D) Total GI transit time, (FIG. 10E) fecal pellet output, (FIG. 15) insulin levels, and (FIG. 10F) colonic transit time, measured in the same mice before and after siK1f11 injection at 4 weeks PI. n=6-20 per condition for each experiment. *p<0.05, **p<0.01 (siK1f11 versus no injection in HFHSD fed mice). These data demonstrated a significant improvement in GI function in mice receiving treatment with siK1f11.

Example 5: Treatment of Obesity by KLF11 Inhibition

Figure 11A:
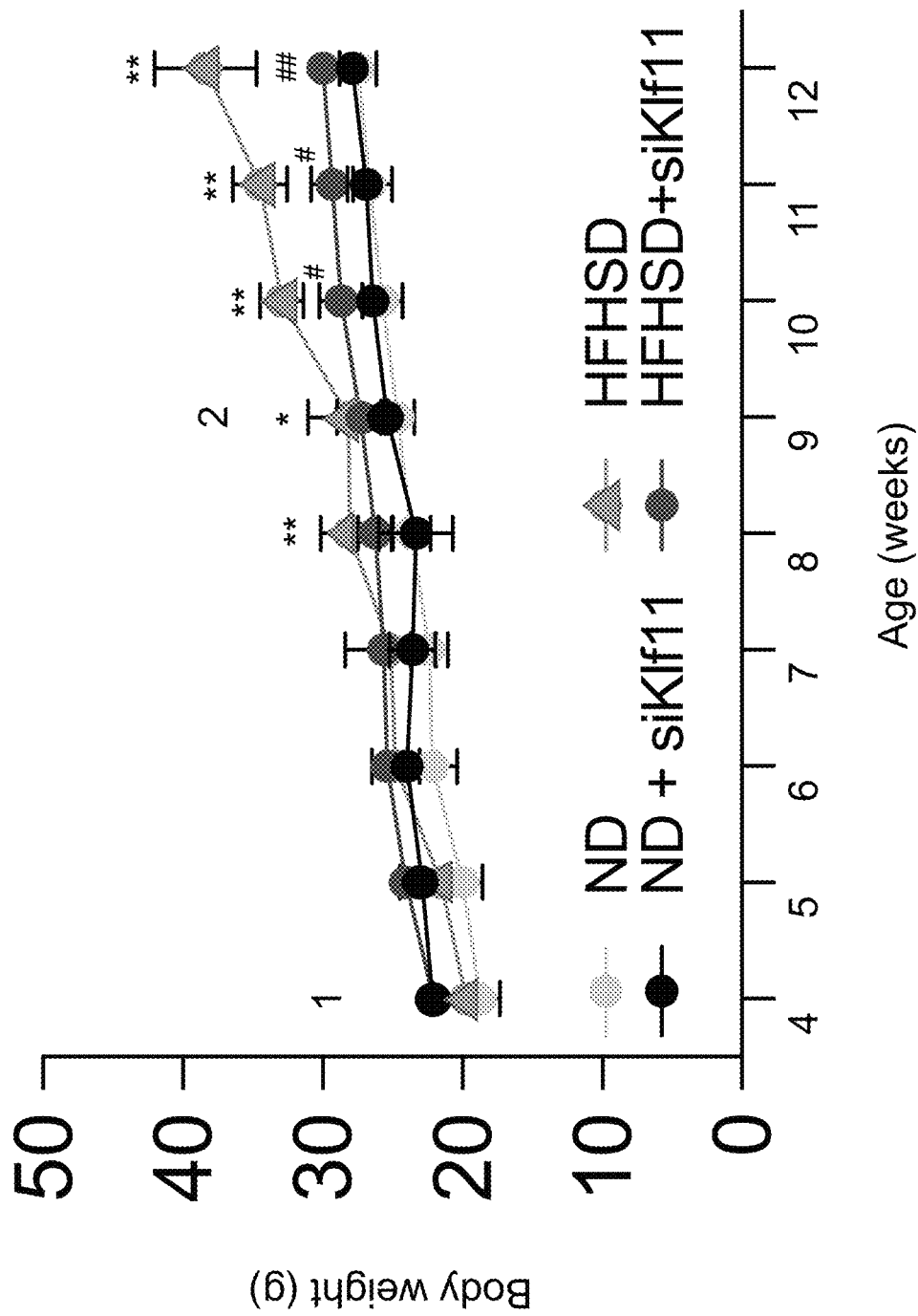
FIGS. 11A-11B depict siK1fl1 protecting against the development of obesity and/or diabetes in mice fed a HFHSD or a ND.
Figure 11B:
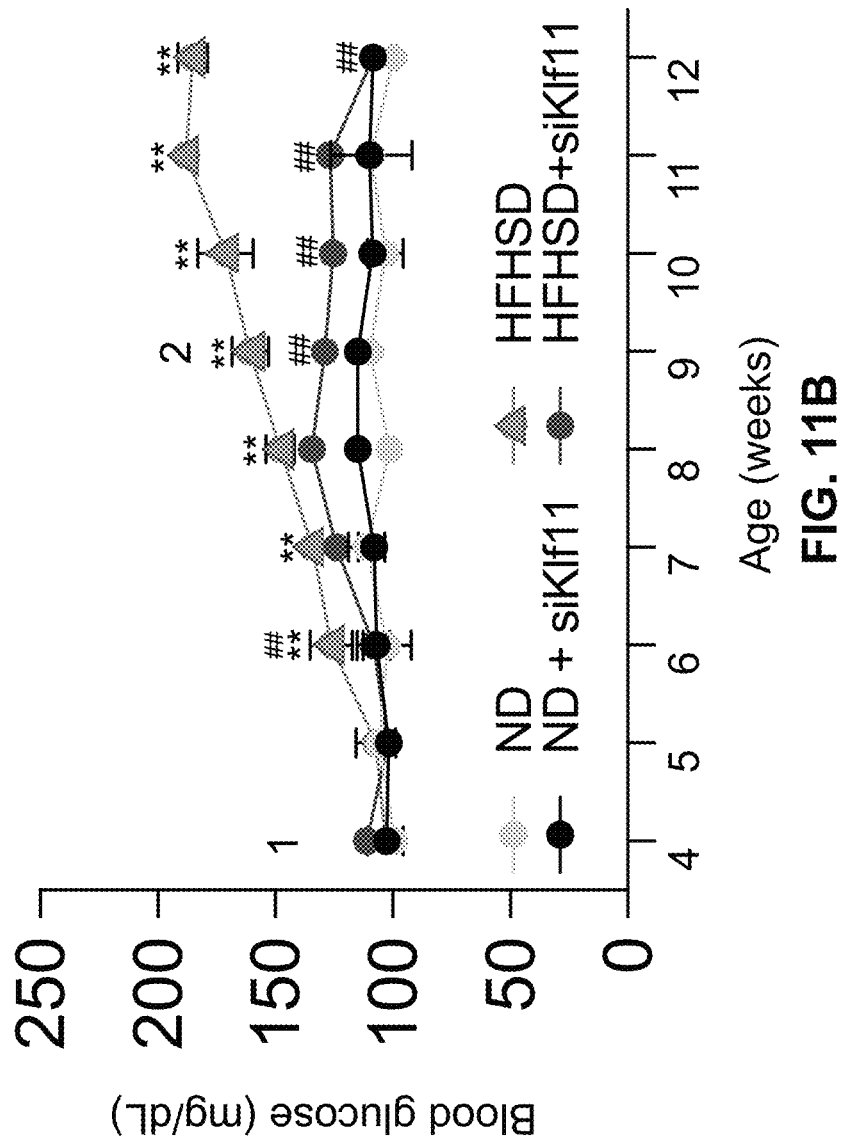

FIGS. 11A-11B depict siK1f11 protects against the development of obesity and/or diabetes in mice fed a HFHSD or a ND. Male C57 mice were injected twice at 4 weeks and 9 weeks (denoted 1 and 2 on the graphs) with the siK1f11 mix or given no injection, and then fed a HFHSD or ND. (FIG. 11A) Body weight was then assessed weekly for the duration of the study. While mice fed a HFHSD showed a significant gain in body weight as compared to ND control, HFHSD-fed mice that also received siK1f11 had body weight changes that were not statistically different from the ND control. The control group of ND-fed mice receiving siK1f11 also had no statistical difference in body weight to the ND-alone group. (FIG. 11B) In the same study, fasting blood glucose levels were also observed weekly. In HFHSD-fed mice, blood glucose levels, as measured in mg/dL, began to increase starting on week 6 and eventually peaked at just under 200 ng/dL on week 12 while levels in ND-fed mice remained largely stagnant. HFHSD-fed mice receiving siK1fl1 showed slight increases in blood glucose starting on week 7, however blood glucose levels remained largely unchanged until week 11 before falling back to the level observed in ND-fed mice on week 12. Mice receiving both a ND and siK1fl1 had blood glucose levels that were not statistically different form ND-alone mice. n=6 per group. *$p<0.05$ and **$p<0.01$, (HFHSD versus ND fed mice), #$p<0.05$ and ##$p<0.01$ (siK1fl1 versus no injection in HFHSD fed mice). These data demonstrated a dramatic ability of siK1fl1 to prevent the development of obesity and diabetes in mice, even in those fed a HFHSD.

Figure 12A:
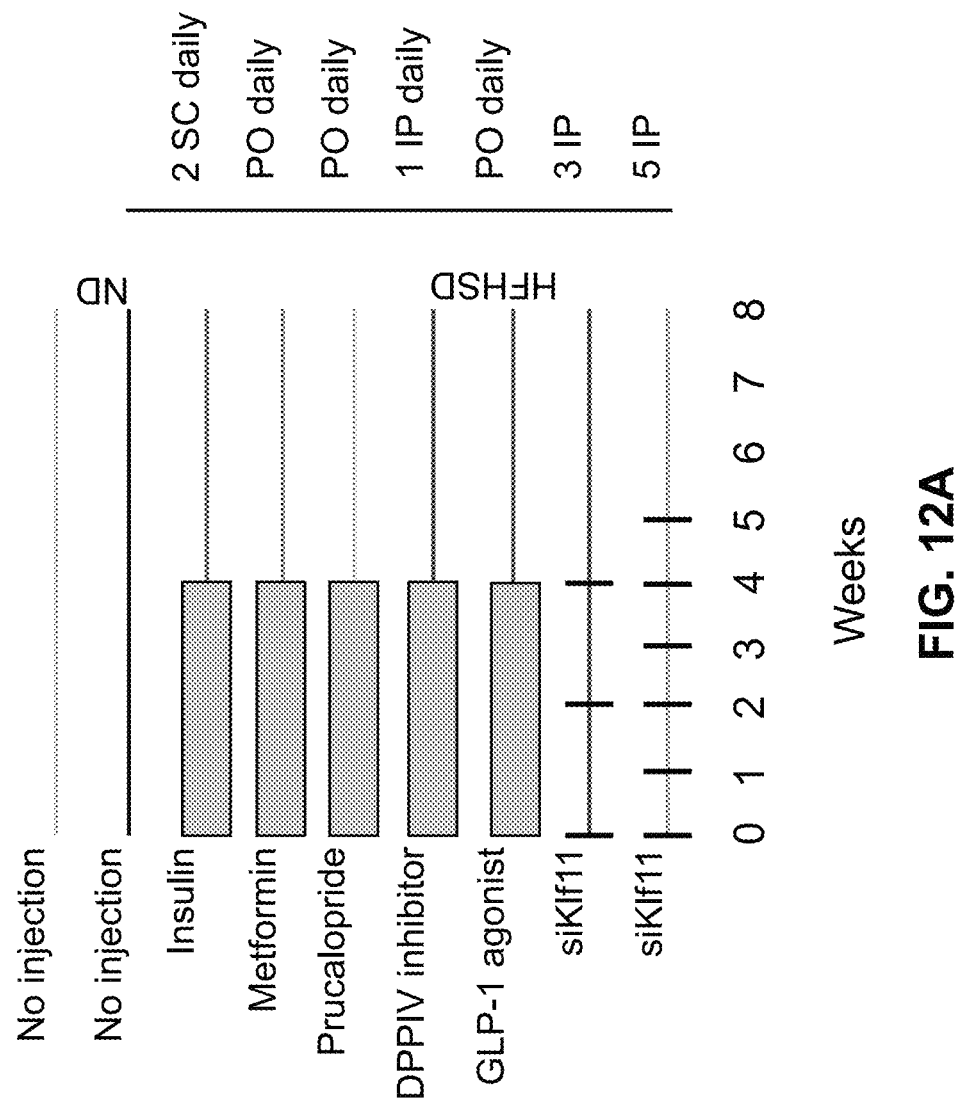
FIGS. 12A-12C illustrate siK1fl1 having a profound and prolonged effect on lowering body weight and blood glucose compared to the indicated anti-diabetic and prokinetic medications.
Figure 12B:
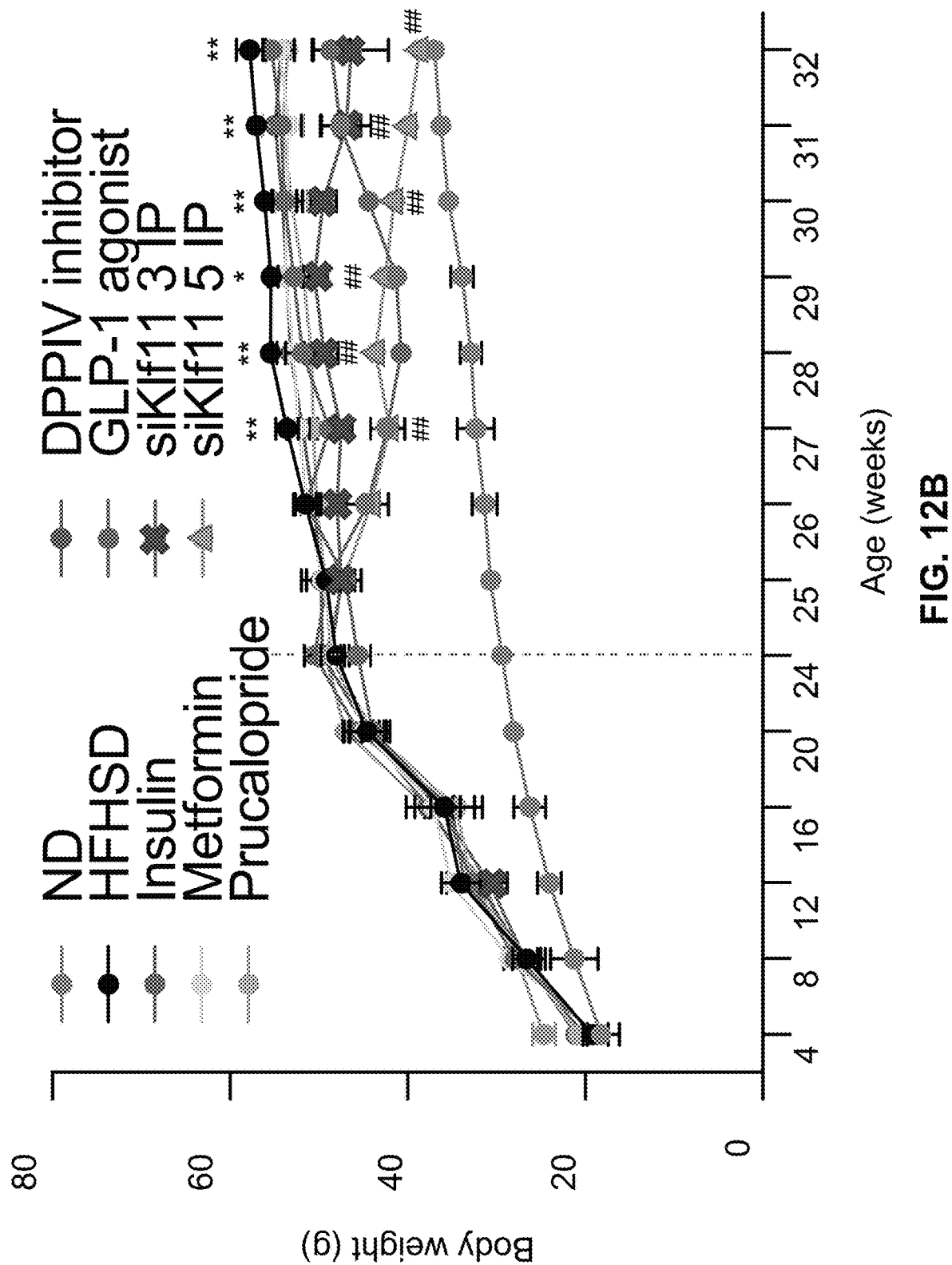
Figure 12C:
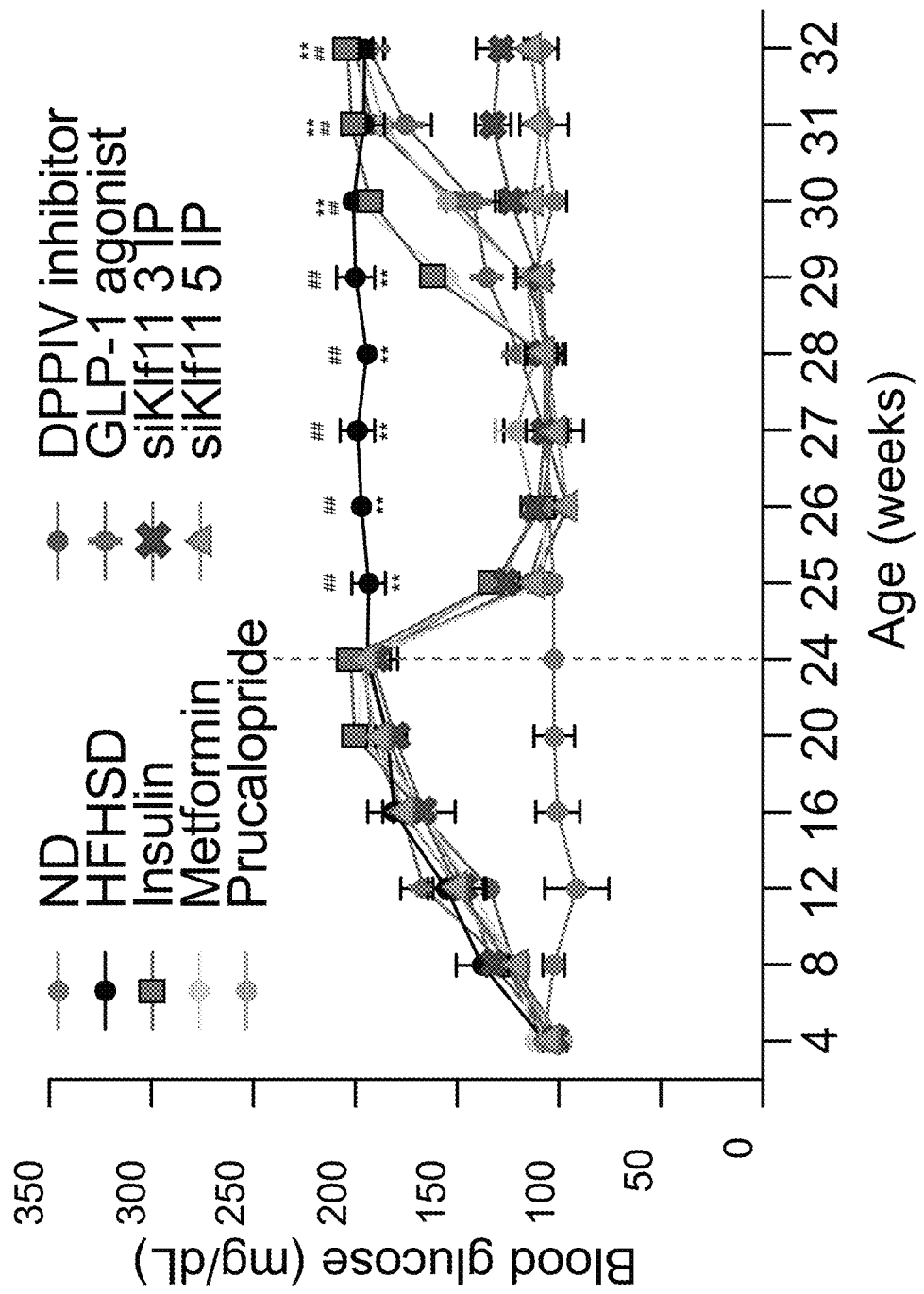
Figure 13B:
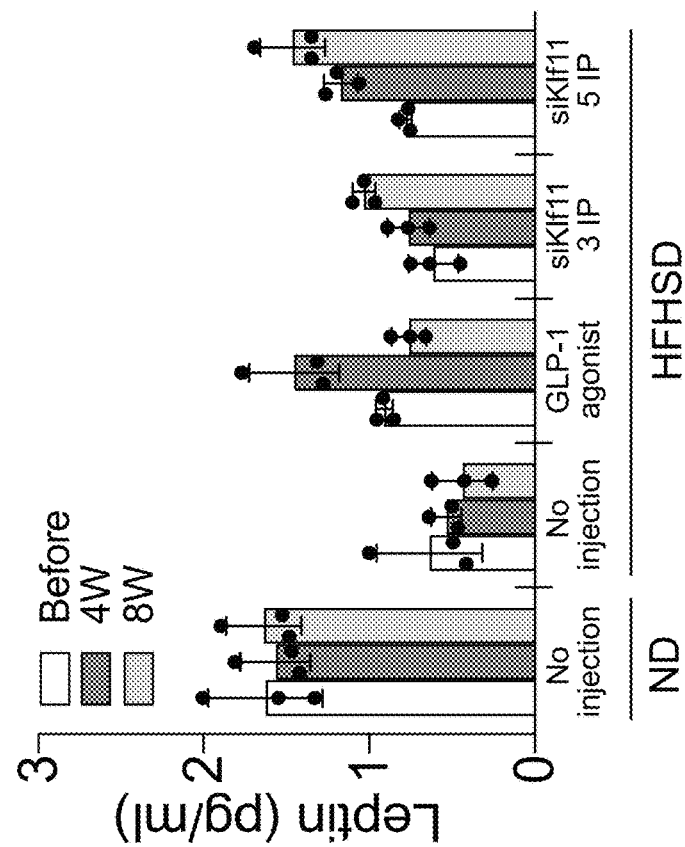
FIGS. 13A-13B illustrate that siK1fl1 has a prolonged effect on the restoration of GLP-1 and leptin in HFHSD-induced diabetic mice compared to GLP-1 agonist.
Figure 13A:
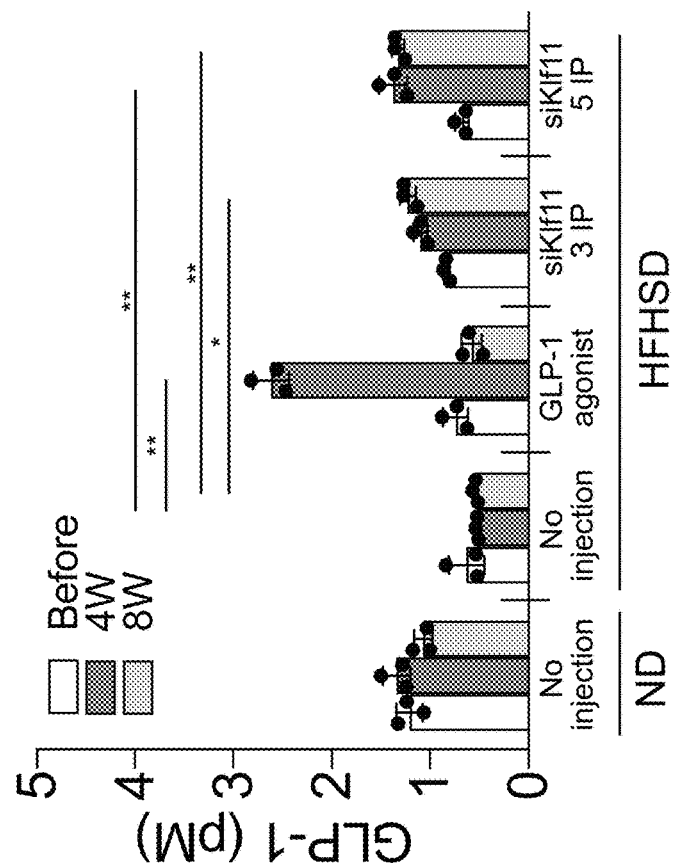
Figure 14:
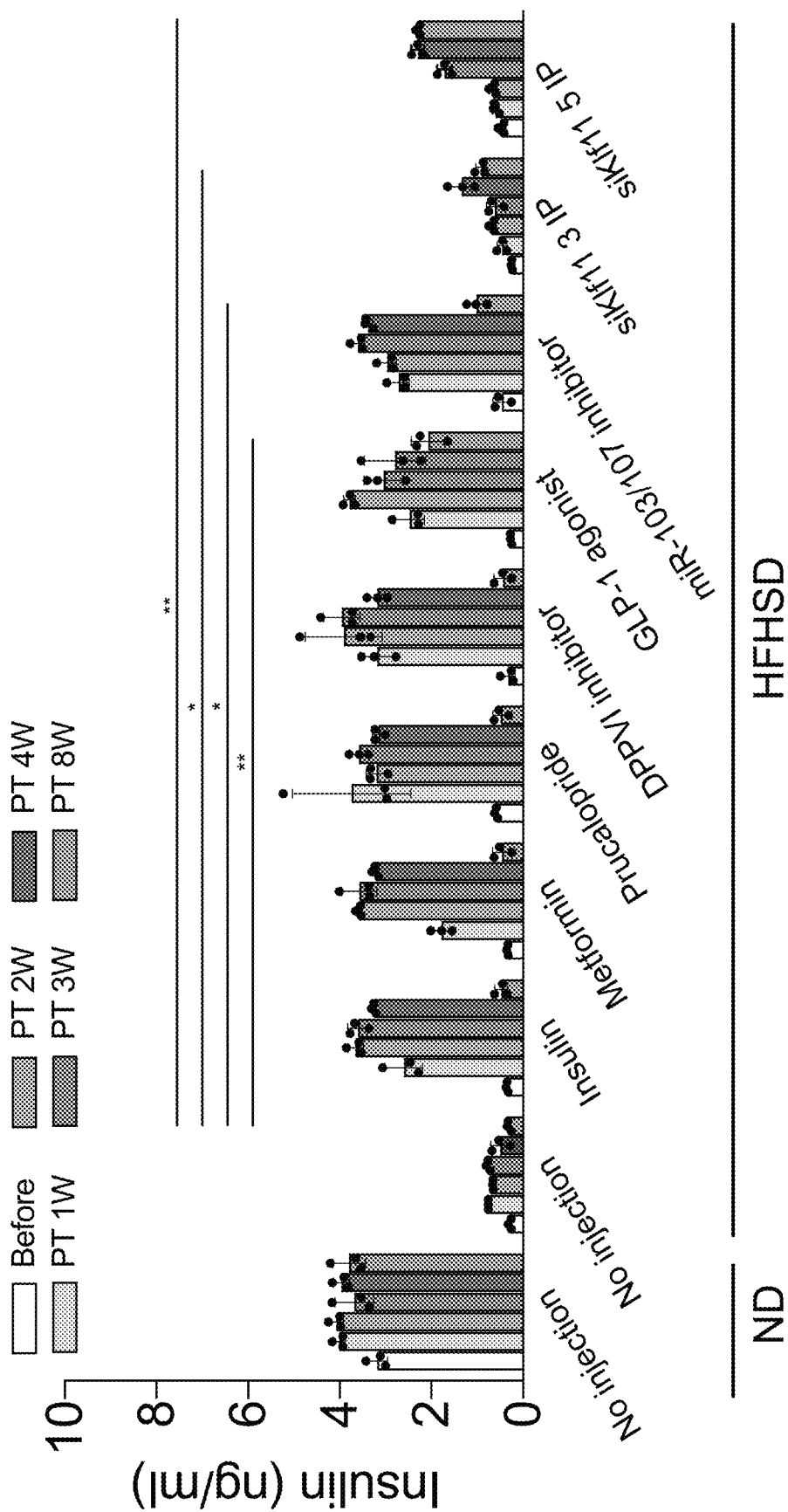
FIG. 14 illustrates siK1fl1 treatment resulting in increased insulin levels in HFHSD-induced diabetic mice compared to the indicated anti-diabetic and prokinetic medications.

The relatively common occurrence of diabetes and diabetes-related diseases has led to the development of a number of drugs designed to counteract aspects of this disease. A comparison of KLF11 inhibition to existing drugs for diabetes and obesity was then conducted in order to compare it to commonly used clinical treatment strategies for these disorders. FIGS. 12A-12C depict siK1fl1 having a profound and prolonged effect on lowering body weight and blood glucose compared to the indicated anti-diabetic and prokinetic medications. (FIG. 12A) A study design of drug effects of siK1fl1, four popular anti-diabetic medications (insulin, metformin, DPPIV inhibitor (sitagliptin), GLP-1 receptor agonist (liraglutide)), and a prokinetic drug (prucalopride). Intraperitoneal injection (IP); oral administration (per os: PO); subcutaneous Injection (SC); 3 IP, 3 intraperitoneal injections; 5 IP, or 5 intraperitoneal injections were performed to administer the medications. (FIGS. 12B and 12C) Body weight and fasting blood glucose measured in mice fed a ND or HFHSD and treated with the siK1fl1 mix, anti-diabetic medications, prokinetic medication, or not treated starting at 24 weeks of age for 8 weeks post treatment. n=3, *$p<0.05$ and $p<0.01$ (siK1fl1 3 IP versus no injection in HFHSD fed mice), #$p<0.05$ and ##$p<0.01$ (siK1fl1 5 IP versus no injection in HFHSD fed mice). (FIGS. 13A and 13B**) GLP-1 and leptin levels were measured before and after treatment at 4 and 8 weeks with either the siK1fl1, GLP-1 agonist or given no injection in male C57 mice fed a ND or a HFHSD. n=3. *$p<0.05$ and $p<0.01$ (siK1fl1 or GLP-1 agonist versus no injection in HFHSD fed mice at 4 weeks and 8 weeks PI). (FIG. 14**) Comparison of insulin levels after 6 hours of fasting in male mice fed a HFHSD (diabetic) before and after treatment at 1 to 4 weeks and 8 weeks with either the siK1fl1, GLP-1 agonist, DPPVI inhibitor, metformin, insulin, prucalopride, or given no injection. n=3. *$p<0.05$ and **$p<0.01$ (drug injection versus no injection in HFHSD fed mice at 8 weeks PI)

Collectively, these data demonstrate the clinical utility of siK1fl1 for the treatment of obesity and diabetes and that.siKlf11 can provide clinical outcomes that are equivalent or better than established medications and shows promise as an investigational drug.

ENUMERATED EMBODIMENTS

The following enumerated embodiments are provided, the numbering of which is not to be construed as designating levels of importance.

Embodiment 1 provides a method of treating diabetes in a subject in need thereof, comprising administering to the subject an effective amount of an inhibitor of KLF11 signaling, thereby treating diabetes.

Embodiment 2 provides the method of embodiment 1, wherein the inhibitor of KLF11 signaling is a small, non-coding RNA molecule.

Embodiment 3 provides the method of embodiment 2, wherein the small, non-coding RNA molecule is selected from the group consisting of an shRNA, an siRNA, and an miRNA.

Embodiment 4 provides the method of embodiment 3, wherein the small, non-coding RNA molecule is an siRNA.

Embodiment 5 provides the method of embodiment 4, wherein the siRNA is encoded by a nucleotide sequence selected from the group consisting of SEQ ID NOs: 1-8, or combinations thereof.

Embodiment 6 provides the method of any one of embodiments 1-5, wherein the diabetes is type 2 diabetes.

Embodiment 7 provides the method of any one of embodiments 1-6, wherein the inhibitor of KLF11 signaling further comprises a pharmaceutically acceptable carrier or adjuvant.

Embodiment 8 provides a method of reducing body weight in a subject in need thereof, comprising administering an effective amount of an inhibitor of KLF11 signaling, thereby reducing the body weight in the subject.

Embodiment 9 provides a method of reducing blood glucose in a subject in need thereof, the method comprising administering an effective amount of an inhibitor of KLF11 signaling, thereby lowering blood glucose in the subject.

Embodiment 10 provides a method for increasing insulin sensitivity in a subject in need thereof, comprising administering an effective amount of an inhibitor of KLF11 signaling, thereby increasing insulin sensitivity.

Embodiment 11 provides the method of any one of embodiments 8-10, wherein the inhibitor of KLF11 signaling is a small, non-coding RNA molecule.

Embodiment 12 provides the method of embodiment 11, wherein the small, non-coding RNA molecule is selected from the group consisting of an shRNA, an siRNA, and an miRNA.

Embodiment 13 provides the method of embodiment 12, wherein the small, non-coding RNA molecule is an siRNA.

Embodiment 14 provides the method of embodiment 13, wherein the siRNA is encoded by a nucleotide sequence selected from the group consisting of SEQ ID NOs: 1-8 or combinations thereof.

Embodiment 15 provides the method of any one of embodiments 8-14, wherein the inhibitor of KLF11 signaling further comprises a pharmaceutically acceptable carrier or adjuvant.

Embodiment 16 provides a method of treating gastrointestinal disease in a subject in need thereof, comprising administering an effective amount of an inhibitor of KLF11 signaling, thereby treating gastrointestinal disease in the subject.

Embodiment 17 provides the method of embodiment 16, wherein the inhibitor of KLF11 signaling is a small, non-coding RNA molecule.

Embodiment 18 provides the method of embodiment 17, wherein the small, non-coding RNA molecule is selected from the group consisting of an shRNA, an siRNA, and an miRNA.

Embodiment 19 provides the method of embodiment 18, wherein the small, non-coding RNA molecule is an siRNA.

Embodiment 20 provides the method of embodiment 19, wherein the siRNA is encoded by a nucleotide sequence selected from the group consisting of SEQ ID NOs: 1-8 or combinations thereof.

Embodiment 21 provides the method of any one of embodiments 16-20, wherein the gastrointestinal disease is selected from the group consisting of gastroparesis, functional gastrointestinal disorder, functional gastrointestinal motility disorder and intestinal pseudo obstruction.

Embodiment 22 provides the method of embodiment 21, wherein the functional gastrointestinal disorder is selected from the group consisting of irritable bowel syndrome, functional constipation and unspecified functional bowel disorder.

Embodiment 23 provides a composition comprising an inhibitor of KLF11 signaling and a pharmaceutically acceptable carrier or adjuvant.

Embodiment 24 provides the composition of embodiment 23, wherein the inhibitor of KLF11 signaling is a small, non-coding RNA molecule.

Embodiment 25 provides the composition of embodiment 24, wherein the small, non-coding RNA molecule is selected from the group consisting of an shRNA, an siRNA, and an miRNA.

Embodiment 26 provides the composition of embodiment 25, wherein the siRNA is encoded by a nucleotide sequence selected from the group consisting of SEQ ID NOs: 1-8 or combinations thereof.

OTHER EMBODIMENTS

The recitation of a listing of elements in any definition of a variable herein includes definitions of that variable as any single element or combination (or sub combination) of listed elements. The recitation of an embodiment herein includes that embodiment as any single embodiment or in combination with any other embodiment or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

---

What is claimed is:

1. A method of treating type-2 diabetes in a subject in need thereof, comprising administering to the subject an effective amount of an inhibitor of Kruppel-like factor 11 (KLF11) signaling, thereby treating type-2 diabetes; wherein the inhibitor is an siRNA encoded by a nucleotide sequence selected from the group consisting of SEQ ID NOs: 7 and 8.

2. The method of claim 1, wherein the inhibitor of KLF11 signaling further comprises a pharmaceutically acceptable carrier or adjuvant.

* * * * *